US008159214B2

(12) United States Patent
Uchiyama et al.

(10) Patent No.: US 8,159,214 B2
(45) Date of Patent: Apr. 17, 2012

(54) POSITION DETECTING SYSTEM

(75) Inventors: Akio Uchiyama, Yokohama (JP); Atsushi Kimura, Akiruno (JP)

(73) Assignee: Olympus Medical Systems Corp., Tokyo (JP)

(*) Notice: Subject to any disclaimer, the term of this patent is extended or adjusted under 35 U.S.C. 154(b) by 440 days.

(21) Appl. No.: 12/399,260

(22) Filed: Mar. 6, 2009

(65) Prior Publication Data

US 2009/0237073 A1 Sep. 24, 2009

(30) Foreign Application Priority Data

Mar. 24, 2008 (JP) ................. 2008-076646

(51) Int. Cl.
*G01B 7/14* (2006.01)
(52) U.S. Cl. ......... 324/207.22; 324/207.13; 324/207.16; 324/207.23; 600/424; 128/899
(58) Field of Classification Search ............. 324/207.15, 324/524, 207.22, 207.16
See application file for complete search history.

(56) References Cited

U.S. PATENT DOCUMENTS

| | | | | |
|---|---|---|---|---|
| 5,353,807 A * | 10/1994 | DeMarco | | 600/585 |
| 5,680,106 A * | 10/1997 | Schrott et al. | | 340/10.33 |
| 6,474,341 B1 * | 11/2002 | Hunter et al. | | 128/899 |
| 6,512,941 B1 * | 1/2003 | Weiss et al. | | 600/410 |
| 7,162,293 B2 * | 1/2007 | Weiss | | 600/411 |
| 7,182,089 B2 * | 2/2007 | Ries | | 128/899 |
| 7,623,904 B2 * | 11/2009 | Uchiyama et al. | | 600/424 |
| 7,696,876 B2 * | 4/2010 | Dimmer et al. | | 340/572.1 |
| 7,697,970 B2 * | 4/2010 | Uchiyama et al. | | 600/407 |
| 7,711,408 B2 * | 5/2010 | Uchiyama et al. | | 600/424 |
| 7,751,866 B2 * | 7/2010 | Aoki et al. | | 600/424 |
| 2005/0195084 A1 | 9/2005 | Dimmer et al. | | |
| 2007/0244388 A1 | 10/2007 | Sato et al. | | |

FOREIGN PATENT DOCUMENTS

| | | |
|---|---|---|
| JP | 2003-275170 | 9/2003 |
| JP | 2004-121733 | 4/2004 |
| JP | 2004-529718 | 9/2004 |
| JP | 2007-054246 | 3/2007 |
| WO | WO 2007/003913 A2 | 1/2007 |
| WO | WO 2007/074888 A1 | 7/2007 |

OTHER PUBLICATIONS

WO 02/095351 A3, dated Nov. 28, 2002 (Abstract and Search Report only).

* cited by examiner

*Primary Examiner* — Richard Isla Rodas
(74) *Attorney, Agent, or Firm* — Scully, Scott, Murphy & Presser, P.C.

(57) ABSTRACT

A position detecting system includes a magnetic field generator, a detecting body, a magnetic field detector, a position/direction calculating unit, and a control unit. The magnetic field generator generates a magnetic field in a three-dimensional space. The detecting body is put into the three-dimensional space, and includes a resonance circuit for generating a resonance magnetic field. The position/direction calculating unit calculates a position/direction of the detecting body. If the resonance circuit is in the non-resonant state, the magnetic field detector detects an environmental magnetic field, and the control unit updates detection data of the environmental magnetic field. If the resonance circuit is in the resonant state, the magnetic field detector detects the spatial magnetic field in the three-dimensional space. The position/direction calculating unit executes processing using the detection data of the spatial magnetic field and updated detection data of the environmental magnetic field.

18 Claims, 17 Drawing Sheets

POSITION DETECTING SYSTEM

CROSS-REFERENCE TO RELATED APPLICATIONS

This application is based upon and claims the benefit of priority from Japanese Patent Application No. 2008-076646, filed Mar. 24, 2008, the entire contents of which are incorporated herein by reference.

BACKGROUND OF THE INVENTION

1. Field of the Invention

The present invention relates to a position detecting system for detecting a position of a detecting body by applying a magnetic field to the detecting body which incorporates therein a resonance circuit (hereinafter, referred to as the "LC resonance circuit") composed of a coil and a capacitor to detect a magnetic field (hereinafter, referred to the "resonance magnetic field") emitted by the LC resonance circuit of the detecting body in response to the applied magnetic field.

2. Description of the Related Art

Conventionally, there has been proposed a position detecting system for detecting a position of a detecting body incorporating therein an LC resonance circuit, by detecting a magnetic field. The position detecting system of magnetic field detection type is usually provided with a magnetic field generating coil for generating a magnetic field in three-dimensional space, and a plurality of magnetic field detecting coils for detecting the magnetic field in the three-dimensional space, wherein the system applies the magnetic field of the magnetic field generating coil to the LC resonance circuit in the detecting body introduced into the three-dimensional space to thereby detect a resonance magnetic field emitted from the LC resonance circuit in the detecting body, by a plurality of magnetic field detecting coils, and thus detects a position of the detecting body in the three-dimensional space based on a magnetic field strength of the detected resonance magnetic field.

Here, when detecting the magnetic field in the three-dimensional space where the detecting body exists, the plurality of magnetic field detecting coils will detect not only the resonance magnetic field of the detecting body, but also an environmental magnetic field, such as a magnetic field of the magnetic field generating coil and the like. For this reason, the position detecting system removes, using subtraction processing or the like, a magnetic field strength of the environmental magnetic field from the magnetic field strength of the magnetic field in the three-dimensional space detected by the magnetic field detecting coil to thereby acquire the magnetic field strength of the resonance magnetic field of the detecting body. It is to be noted that the aforementioned position detecting system generates the magnetic field of the magnetic field generating coil in the three-dimensional space in a state where the detecting body does not exist, and detects by the plurality of magnetic field detecting coils the magnetic field generated in the three-dimensional space, namely, the environmental magnetic field, such as the magnetic field of the magnetic field generating coil and the like to thereby acquire the magnetic field strength of the environmental magnetic field in the three-dimensional space.

Such a position detecting system includes a system that applies a magnetic field to a detecting body, which is a capsule medical device that is thrown into a body of a subject being tested to thereby conduct a medical practice, detects an induction field (namely, resonance magnetic field), which is inducted by the applied magnetic field and emitted by the detecting body, and detects a position of the detecting body (capsule medical device) based on the detected induction field (for example, refer to Japanese Patent Application Laid-Open No. 2007-54246).

SUMMARY OF THE INVENTION

According to one aspect of the present invention, a position detecting system includes a magnetic field generator that generates a magnetic field in a three-dimensional space, a detecting body that incorporates a resonance circuit for resonating with the magnetic field of the magnetic field generator to generate a resonance magnetic field, a current bypass circuit connected to the resonance circuit in parallel to form an alternative path of a current in the resonance circuit, and a resonance control circuit for controlling a current flow through the current bypass circuit to switch a resonant state and a non-resonant state of the resonance circuit, and is introduced into the three-dimensional space, a magnetic field detector that detects an environmental magnetic field, being a magnetic field in the three-dimensional space excluding the resonance magnetic field, and including at least a magnetic field of the magnetic field generator if the resonance circuit is in the non-resonant state, and detects a spatial magnetic field in the three-dimensional space including the environmental magnetic field and the resonance magnetic field if the resonance circuit is in the resonant state, a position/direction calculating unit that performs position/direction calculating processing for calculating a position and a direction of the detecting body based on the detection data of the resonance magnetic field obtained by subtracting the detection data of the environmental magnetic field from the detection data of the spatial magnetic field, and a control unit that acquires detection data of the environmental magnetic field to perform update processing on the detection data of the environmental magnetic field if the resonance circuit is in the non-resonant state, acquires the detection data of the spatial magnetic field if the resonance circuit is in the resonant state, and causes the position/direction calculating unit to execute the position/direction calculating processing using the detection data of the spatial magnetic field thus acquired and the detection data of the environmental magnetic field which is subjected to the update processing.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, a position detecting system which is the best mode for carrying out the present invention will be described. It is to be noted that in the following, a capsule medical device which is introduced into the inside of a subject, such as a patient or the like to thereby capture an image inside an internal organ of the subject (hereinafter, it may also be called the "image in the body") will be illustrated as one example of a detecting body of a position detecting system in accordance with the present invention, and a position detecting system for detecting a position of the capsule medical device which is the detecting body will be described, but the present invention is not limited by the embodiments.

Figure 1:
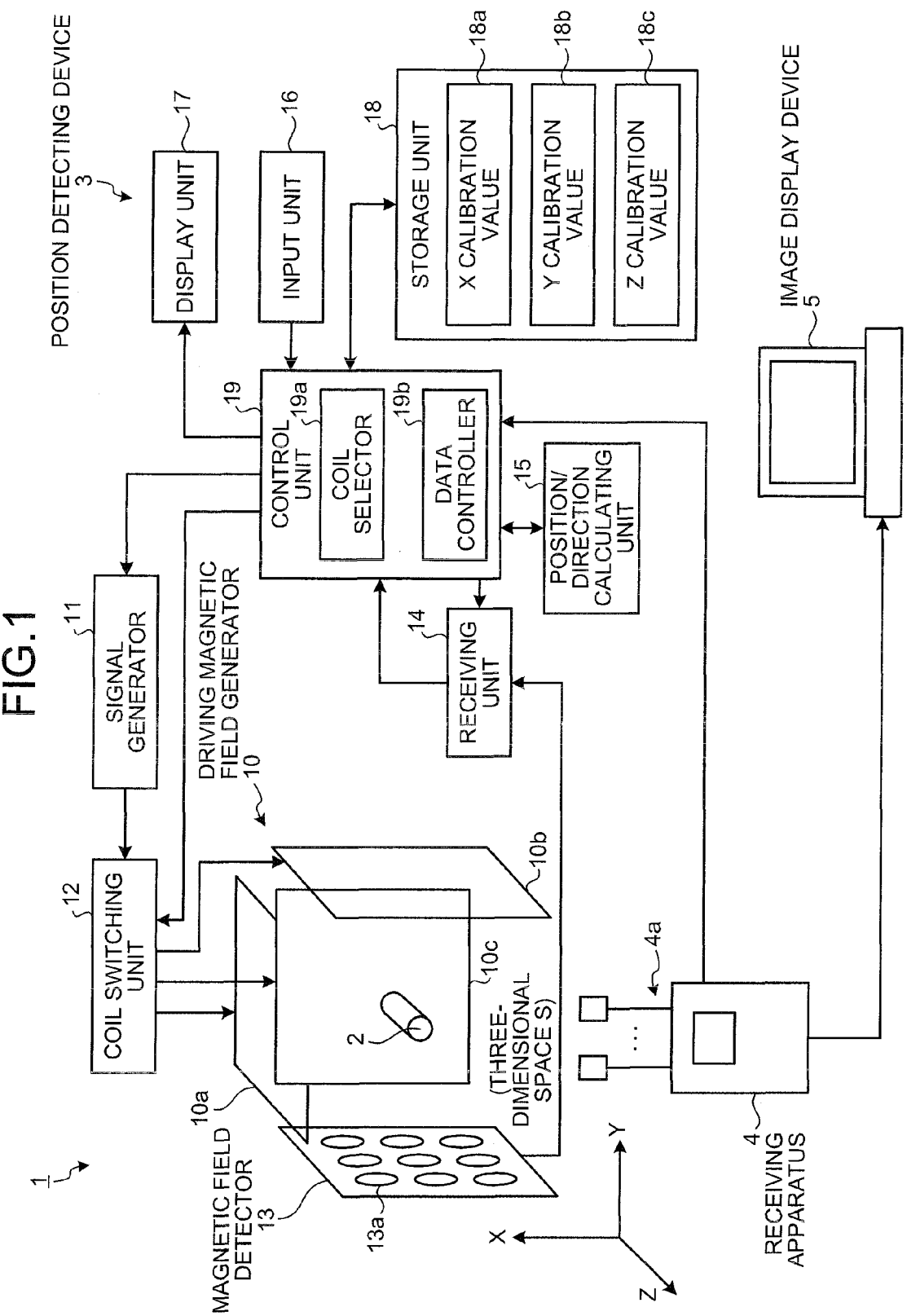
FIG. 1 is a block diagram schematically showing one configuration example of a position detecting system in accordance with a first embodiment of the present invention.

FIG. 1 is a block diagram schematically showing one configuration example of a position detecting system in accordance with a first embodiment of the present invention. As shown in FIG. 1, a position detecting system 1 in accordance with the first embodiment is provided with a capsule medical device 2 for capturing an image in a body of a subject, such as a patient or the like, a position detecting device 3 for detecting a position and the like of the capsule medical device 2 inside the subject (namely, three-dimensional space S), a receiving apparatus 4 for receiving radio signals of the image in the body or the like captured by the capsule medical device 2, and an image display device 5 for displaying the image in the body and the like received by the receiving apparatus 4. In the position detecting system 1, the position detecting device 3 is provided with a driving magnetic field generator 10 for generating a driving magnetic field that induces a resonance magnetic field from the capsule medical device 2, a signal generator 11 for generating an alternating current signal applied to the driving magnetic field generator 10, a coil switching unit 12 for switching magnetic field generating coils (drive coils 10a, 10b, and 10c which will be hereinafter described) of the driving magnetic field generator 10, a magnetic field detector 13 for detecting the resonance magnetic field or the like from the capsule medical device 2, and a receiving unit 14 for receiving magnetic field detection data obtained by the magnetic field detector 13. In addition, the position detecting device 3 is provided with a position/direction calculating unit 15 for calculating a position and a direction of the capsule medical device 2 in the three-dimensional space S, an input unit 16 for receiving a variety of information, a display unit 17 for displaying information, including the position and direction, and the like of the capsule medical device 2 in the three-dimensional space S (specifically, inside of the subject), a storage unit 18 for storing information and the like required for calculation processing of the position and direction of the capsule medical device 2, and a control unit 19 for controlling each component unit of the position detecting device 3.

The capsule medical device 2 is a capsule medical device for acquiring the image in the body of the subject (one example of in-vivo information of the subject), and has an imaging function and a wireless communication function. The capsule medical device 2 is introduced into the inside of a digestive tract of a subject such as a patient (not shown), sequentially captures the image in the body while moving the inside of the digestive tract of the subject, and sequentially wirelessly transmits an image signal including the image in the body and the like to the receiving apparatus 4 outside the subject at each time of capturing the image. In addition, the capsule medical device 2 has a function to generate a resonance magnetic field according to action of the driving magnetic field emitted by the driving magnetic field generator 10 of the position detecting device 3. Incidentally, a detailed configuration of the capsule medical device 2 will be hereinafter described.

The receiving apparatus 4 receives the image in the body or the like captured by the capsule medical device 2 inside the subject. Specifically, the receiving apparatus 4 has a plurality of receiving antennas 4a. A plurality of receiving antennas 4a are distributedly arranged on a body surface of the subject, into the inside of the body of which the capsule medical device 2 is introduced, and captures radio signals from the capsule medical device 2 inside the subject. The receiving apparatus 4 receives the radio signals from the capsule medical device 2 via the plurality of receiving antennas 4a, and performs demodulation processing or the like to the radio signals thus received to acquire the image signal from the capsule medical device 2. The receiving apparatus 4 transmits a synchronizing signal included in the acquired image signal to the control unit 19 as a timing signal at each time of acquiring the image signal. Meanwhile, the receiving apparatus 4 sequentially transmits the acquired image signal, namely, the image signal including the image in the body of the subject, to the image display device 5.

The image display device 5 has a configuration of a workstation or the like for displaying a variety of information such as a set of images in the body and the like captured by the capsule medical device 2 inside the subject. The image display device 5 acquires the image signal from the capsule medical device 2 via the receiving apparatus 4, and displays a variety of information such as the image in the body of the subject corresponding to the acquired image signal at each time of acquiring the image. In addition, the image display device 5 has various processing functions for the user such as a doctor or a nurse to observe (examine) the image in the body of the subject to thereby diagnose the subject. It is to be noted that a variety of information to be displayed by the image display device 5 includes, for example, patient information such as a patient name and a patient ID for specifying the subject, examination information such as an examination ID and an examination date for specifying an examination for the subject, and the like, other than the set of images in the body of the subject.

The driving magnetic field generator 10 generates a magnetic field (driving magnetic field) for inducing the resonance magnetic field from the capsule medical device 2 inside the subject, in the three-dimensional space S where the subject (not shown) which has introduced the capsule medical device 2 into the inside of the body thereof, is located. Specifically, the driving magnetic field generator 10 is achieved by combining the drive coils 10a to 10c that respectively generate driving magnetic fields in each axial direction of a three-axis Cartesian coordinate system (hereinafter, referred to as the "absolute coordinate system") for defining the three-dimensional space S.

The drive coil 10a generates an alternating magnetic field in the X-axis direction of the absolute coordinate system based on the alternating current signal from the coil switching unit 12, and emits the generated alternating magnetic field to the three-dimensional space S as a driving magnetic field in the X-axis direction. The drive coil 10b generates an alternating magnetic field in the Y-axis direction of the absolute coordinate system based on the alternating current signal from the coil switching unit 12, and emits the generated alternating magnetic field to the three-dimensional space S as a driving magnetic field in the Y-axis direction. The drive coil 10c generates an alternating magnetic field in the Z-axis direction of the absolute coordinate system based on the alternating current signal from the coil switching unit 12, and emits the generated alternating magnetic field to the three-dimensional space S as a driving magnetic field in the Z-axis direction. The driving magnetic fields generated by the drive coils 10a to 10c are applied to the capsule medical device 2 in the three-dimensional space S to induce the resonance magnetic field from the capsule medical device 2.

It is to be noted that the absolute coordinate system may be a three-axis Cartesian coordinate system defined to the aforementioned driving magnetic field generator 10, may be a three-axis Cartesian coordinate system defined to the subject which includes the capsule medical device 2 inside the digestive tract, or may be a three-axis Cartesian coordinate system defined to a support member (not shown) such as a bed for supporting the subject.

The signal generator 11 generates an alternating current signal to be applied to the driving magnetic field generator 10. Specifically, the signal generator 11 generates an alternating current signal applied to a drive coil selected by the control unit 19 among the drive coils 10a to 10c, and outputs the generated alternating current signal to the coil switching unit 12.

The coil switching unit 12 is for switching a drive coil for emitting the driving magnetic field in the three-dimensional space S. Specifically, the coil switching unit 12 is achieved using a switching circuit or the like, and switches a drive coil that emits the driving magnetic field in the three-dimensional space S among the drive coils 10a to 10c of the driving magnetic field generator 10 based on the control of the control unit 19. In this case, the coil switching unit 12 connects a drive coil selected by the control unit 19 among the drive coils 10a to 10c to the signal generator 11, and outputs an alternating current signal from the signal generator 11 to the selected drive coil. As a result of this, the coil switching unit 12 supplies an alternating current required for generating the driving magnetic field to the selected drive coil (any one of the drive coils 10a to 10c).

The magnetic field detector 13 detects the magnetic field generated in the three-dimensional space S. Specifically, the magnetic field detector 13 is achieved using a plurality of detecting coils 13a arranged, for example, in a grid-pattern, and detects the magnetic field in the three-dimensional space S by a plurality of the detecting coils 13a. Whenever the magnetic field detector 13 detects the magnetic field, it transmits obtained magnetic field detection data to the receiving unit 14. It is to be noted that the magnetic field in the three-dimensional space S detected by the magnetic field detector 13 includes a resonance magnetic field from the capsule medical device 2, a magnetic field in the three-dimensional space S excluding this resonance magnetic field (hereinafter, referred to as the "environmental magnetic field"), and all the magnetic fields in the three-dimensional space S including the resonance magnetic field and the environmental magnetic field (hereinafter, referred to as the "spatial magnetic field"). In addition, this environmental magnetic field in the three-dimensional space S is a magnetic field including at least the driving magnetic field by the driving magnetic field generator 10, and includes, for example, earth magnetism, a magnetic field produced by external devices other than the driving magnetic field generator 10, and the like, other than this driving magnetic field. Incidentally, the number of arrangements of the detecting coil 13a in the magnetic field detector 13 is not limited to nine, but may just be a plurality of detecting coils. In addition, the arrangement of the plurality of detecting coils 13a is not limited to the grid-pattern, but desired arrangements may be used.

The receiving unit 14 receives the magnetic field detection data detected by the magnetic field detector 13, and performs predetermined signal processing, such as amplification processing, digitization processing, FFT processing, and the like, to the received magnetic field detection data at each time of receiving the magnetic field detection data. The receiving unit 14 sequentially transmits to the control unit 19 the magnetic field detection data subjected to the signal processing, based on the control of the control unit 19.

The position/direction calculating unit 15 calculates the position and direction of the capsule medical device 2 inside the subject (namely, inside the three-dimensional space S) based on the aforementioned magnetic field detection data of the magnetic field detector 13. Specifically, the position/direction calculating unit 15 acquires the magnetic field detection data (for example, magnetic field strength detection value) of the spatial magnetic field inside the three-dimensional space S, and a calibration value corresponding to the drive coil in a driving state, from the control unit 19 at a timing when an operation is permitted by control unit 19), and calculates the three-dimensional position and direction of the capsule medical device 2 inside the three-dimensional space S based on thus acquired magnetic field strength detection value of the spatial magnetic field and calibration value. Whenever the position/direction calculating unit 15 calculates the position and direction of the capsule medical device 2, it sequentially transmits the obtained calculation result to the control unit 19 as position/direction information of the capsule medical device 2.

It is to be noted that the drive coil in the driving state here means a drive coil in a state of emitting the driving magnetic field among the drive coils 10a to 10c of the aforementioned driving magnetic field generator 10. Meanwhile, the calibration value means a reference value for extracting the magnetic field detection data of the resonance magnetic field from the capsule medical device 2, from the magnetic field detection data of the spatial magnetic field inside the three-dimensional space S detected by the magnetic field detector 13, and specifically, it is the magnetic field detection data (for example, magnetic field strength detection value) of the environmental magnetic field in the aforementioned three-dimensional space S. The calibration value includes an X calibration value corresponding to the environmental magnetic field including the driving magnetic field in the X-axis direction emitted by the drive coil 10a, a Y calibration value corresponding to the environmental magnetic field including the driving magnetic field in the Y-axis direction emitted by the drive coil 10b, and a Z calibration value corresponding to the environmental magnetic field including the driving magnetic field in the Z-axis direction emitted by the drive coil 10c.

The input unit 16 is achieved using an input device, such as a keyboard, a mouse, and the like, and inputs various instruction information and the like to the control unit 19 according to an input operation by the user, such as a doctor, a nurse, or the like. It is to be noted that the instruction information inputted by the input unit 16 includes, for example, instruction information for instructing switching of the drive coil in the driving state; instruction information for instructing to display the position/direction information of the capsule medical device 2; instruction information for instructing completion of various operations, such as emission of the driving magnetic field and the like, required for detecting the position and direction of the capsule medical device 2; instruction information for instructing display completion of the position/direction information of the capsule medical device 2; and the like.

The display unit 17 is achieved using various displays, such as a CRT display, a liquid crystal display, or the like, and displays a variety of information instructed to be displayed by the control unit 19. Specifically, the display unit 17 displays information for indicating the position and direction of the capsule medical device 2 inside the subject, and the like. The display unit 17 may display the position and direction of the capsule medical device 2 inside the subject by suitably superimposing and displaying a pattern image visualizing a bodily shape of the subject, a pattern image visualizing the digestive tract of the subject, a pattern image combining these pattern images, a pattern image visualizing an outer shape of the capsule medical device 2, and the like, or may display the position and direction of the capsule medical device 2 inside the subject by a position coordinate, a direction vector, or the like of the capsule medical device 2 in the absolute coordinate system of the three-dimensional space S.

The storage unit 18 is achieved using various memory media that rewritably store information, such as RAM, EEPROM, flash memory, hard disk, or the like. The storage unit 18 stores a variety of information instructed to be stored by the control unit 19, and sends out to the control unit 19 information instructed to be read by the control unit 19 among the stored variety of information. The storage unit 18 stores an X calibration value 18a corresponding to the environmental magnetic field including the driving magnetic field in the X-axis direction generated by the drive coil 10a, a Y calibration value 18b corresponding to the environmental magnetic field including the driving magnetic field in the Y-axis direction generated by the drive coil 10b, and a Z calibration value 18c corresponding to the environmental magnetic field including the driving magnetic field in the Z-axis direction generated by the drive coil 10c, and suitably updates the X calibration value 18a, the Y calibration value 18b, and the Z calibration value 18c, based on the control of the control unit 19.

The control unit 19 controls an operation of each component unit of the position detecting device 3 (specifically, the driving magnetic field generator 10, the signal generator 11, the coil switching unit 12, the receiving unit 14, the position/direction calculating unit 15, the input unit 16, the display unit 17, and the storage unit 18), and controls input and output of signals between respective component units. Specifically, the control unit 19 controls an alternating current signal generating operation of the signal generator 11, a drive coil switching operation of the coil switching unit 12, a display operation of the display unit 17, and the like, based on the instruction information inputted by the input unit 16. The control unit 19 controls the alternating current signal (namely, an energizing amount of the alternating current supplied to the drive coils 10a to 10c) generated by the signal generator 11, and controls the driving magnetic fields of the drive coils 10a to 10c through the control of the alternating current signal.

Additionally, the control unit 19 acquires a timing signal from the receiving apparatus 4, and controls prohibition or execution of position/direction calculation processing of the capsule medical device 2 by the position/direction calculating unit 15 based on the acquired timing signal. The control unit 19 updates the position/direction information of the capsule medical device 2 displayed on the display unit 17 to the up-to-date information, whenever the position/direction calculating processing is executed. In addition, the control unit 19 has a coil selector 19a and a data controller 19b. The coil selector 19a selects a drive coil that should emit the driving magnetic field among the drive coils 10a to 10c of the driving magnetic field generator 10. Specifically, the coil selector 19a acquires magnetic field detection data (namely, magnetic field detection data of the magnetic field detector 13) from the receiving unit 14, and compares the acquired magnetic field detection data with a threshold value previously set. The coil selector 19a selects a drive coil (namely, drive coil that should emit the driving magnetic field) that generates a driving magnetic field suitable for inducing the resonance magnetic field from the capsule medical device 2 among the drive coils 10a to 10c of the driving magnetic field generator 10 based on the result of the comparison processing. The control unit 19 controls the coil switching unit 12 to switch to the drive coil selected by the coil selector 19a among the drive coils 10a to 10c.

The data controller 19b controls selection of the magnetic field detection data of the magnetic field detector 13. Specifically, the data controller 19b sequentially acquires the magnetic field detection data of the magnetic field detector 13 via the receiving unit 14. Meanwhile, the data controller 19b sequentially acquires a timing signal from the receiving apparatus 4 at a predetermined time interval. The data controller 19b determines whether to employ or to discard the magnetic field detection data based on acquisition timing of the timing signals. It is to be noted that the magnetic field detection data employed by the data controller 19b is used as operation data of the aforementioned position/direction calculating processing of the capsule medical device 2 by the position/direction calculating unit 15, or as calibration values (specifically, the X calibration value 18a, the Y calibration value 18b, or the Z calibration value 18c) of the position/direction calculating processing.

Figure 2:
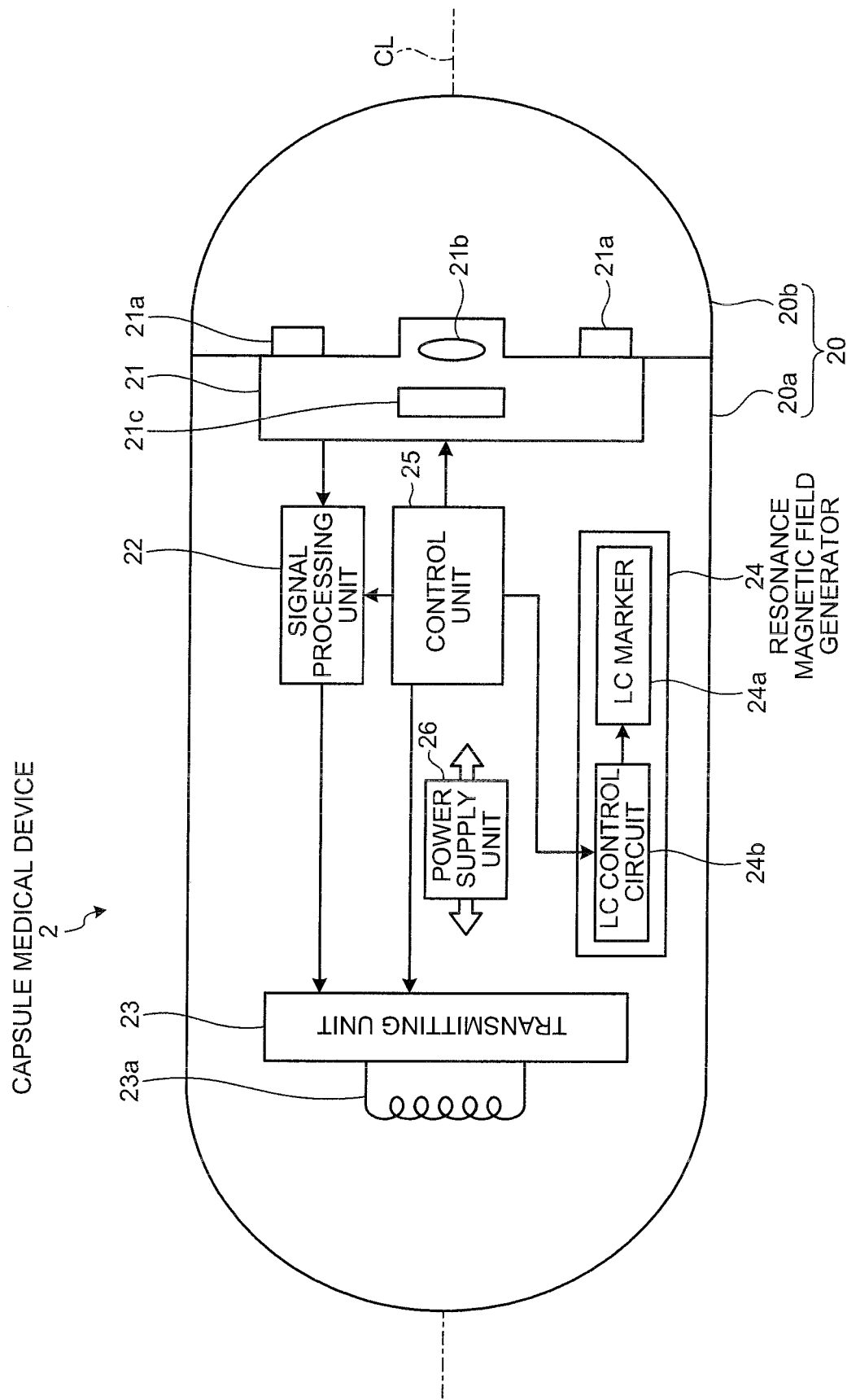
FIG. 2 is a schematic view showing one configuration example of a capsule medical device of the position detecting system in accordance with the first embodiment of the present invention.

Next, a configuration of the capsule medical device 2 of the position detecting system 1 in accordance with the first embodiment of the present invention will be described in detail. FIG. 2 is a schematic view showing one configuration example of the capsule medical device of the position detecting system in accordance with the first embodiment of the present invention. As shown in FIG. 2, the capsule medical device 2 in accordance with the first embodiment is provided with a capsule type case 20 with a size capable of being introduced into the inside of the digestive tract of the subject, an imaging unit 21 for capturing the image in the body of the subject, a signal processing unit 22 for generating an image signal including the image in the body and the like captured by the imaging unit 21, a transmitting unit 23 for wirelessly transmitting the image signal generated by the signal processing unit 22 to the outside, a resonance magnetic field generator 24 for generating a resonance magnetic field in response to the aforementioned driving magnetic field, a control unit 25 for controlling each component unit of the capsule medical device 2, and a power supply unit 26 achieved by a battery or the like.

The capsule type case 20 is a capsule type case formed in a size capable of being introduced into the inside of the digestive tract of the subject, and it is formed by closing the other end (open end) of a cylindrical case 20a, one end of which forms a dome shape, with a dome shape case 20b. The dome shape case 20b is an optical dome transparent to a light (for example, visible light) with a predetermined wavelength band. Meanwhile, the cylindrical case 20a is a case substantially intransparent to a visible light. The imaging unit 21, the signal processing unit 22, the transmitting unit 23, the resonance magnetic field generator 24, the control unit 25, and the power supply unit 26 are fluid-tightly housed inside the capsule type case 20 formed of the cylindrical case 20a and the dome shape case 20b.

It is to be noted that the direction of the capsule medical device 2 to be calculated by the aforementioned position/direction calculating unit 15 is determined by a direction of a longitudinal axis CL of the capsule type case 20 (longitudinal axis direction), and mutually-orthogonal two axes perpendicular to the longitudinal axis CL (namely, radial direction of the capsule type case 20).

The imaging unit 21 is one example of a function executing unit that repeatedly executes a predetermined function at a predetermined time interval, based on the control of the control unit 25. Specifically, the imaging unit 21 is a function executing unit for sequentially capturing the image in the body of the subject, and is provided with an illuminating unit 21a such as an LED, an optical system 21b such as a condenser lens, and a solid-state image sensor 21c. A plurality of illuminating units 21a illuminate an object (specifically, inside of the internal organ of the subject) over the dome shape case 20b, and the optical system 21b condenses reflected lights from the illuminated object to form an optical image of the object on a light receiving surface of the solid-state image sensor 21c. The solid-state image sensor 21c captures the optical image of the object, namely, the image in the body of the subject.

The signal processing unit 22 acquires a signal photoelectrically converted by the solid-state image sensor 21c of the imaging unit 21, and performs predetermined signal processing on the acquired signal to thereby generate an image signal of the subject. The signal processing unit 22 sequentially transmits the image signal of the subject to the transmitting unit 23. It is to be noted that the image signal generated by the signal processing unit 22 includes date of the image in the body of the subject captured by the imaging unit 21, a synchronizing signal (vertical synchronizing signal, horizontal synchronization signal), and the like.

The transmitting unit 23 is provided with a coiled transmission antenna 23a, and wirelessly transmits to the receiving apparatus 4 outside the subject the image signal of the subject using the transmission antenna 23a (refer to FIG. 1). Specifically, the transmitting unit 23 acquires the image signal of the subject from the signal processing unit 22, and performs predetermined modulation processing and the like on the acquired image signal at each time of acquiring the image signal to thereby generate a radio signal including the image signal of the subject. The transmitting unit 23 sequentially transmits the radio signal to the outside via the transmission antenna 23a. The radio signal (namely, image signal of the subject) transmitted by the transmitting unit 23 is received by the receiving apparatus 4 via a plurality of receiving antennas 4a.

The resonance magnetic field generator 24 generates a resonance magnetic field in response to the driving magnetic field (specifically, driving magnetic field in the X-axis direction according to the drive coil 10a, driving magnetic field in the Y-axis direction by the drive coil 10b, or driving magnetic field in the Z-axis direction by the drive coil 10c) of the driving magnetic field generator 10. More specifically, the resonance magnetic field generator 24 is provided with an LC marker 24a and an LC control circuit 24b. The LC marker 24a is achieved using a coil, a capacitor, and the like, and resonates with the driving magnetic field of the driving magnetic field generator 10 to emit a resonance magnetic field in a case of a resonant state. It is to be noted that the resonance magnetic field emitted by the LC marker 24a is an induction field induced by the driving magnetic field of the driving magnetic field generator 10. The LC control circuit 24b controls switching between the resonant state and a non-resonant state of the LC marker 24a based on the control of the control unit 25 to thereby control generation timing and stop timing of the resonance magnetic field of the LC marker 24a. Specifically, the LC control circuit 24b releases the resonant state of the LC marker 24a at the timing (for example, timing of capturing the image in the body) instructed by the control unit 25 to thereby switch it to the non-resonant state, and maintains the non-resonant state of the LC marker 24a during a predetermined period. Subsequently, the LC control circuit 24b switches the non-resonant state of the LC marker 24a to the resonant state thereof.

The control unit 25 controls each component unit (the imaging unit 21, the signal processing unit 22, the transmitting unit 23, and the resonance magnetic field generator 24) of the capsule medical device 2, and controls input and output of signals between respective component units. Specifically, the control unit 25 controls the imaging unit 21 to sequentially capture the image in the body of the subject at a predetermined time interval (for example, at 0.5 seconds interval), and controls the signal processing unit 22 and the transmitting unit 23 to wirelessly transmit sequentially to the outside the image signal including the image in the body of the subject and the like captured by the imaging unit 21. Further, whenever the control unit 25 makes the imaging unit 21 capture the image in the body of the subject, it controls the LC control circuit 24b to release the resonant state of the LC marker 24a (namely, it switches the LC marker 24a from the resonant state to the non-resonant state) at the timing of capturing the image in the body. Namely, the control unit 25 controls the LC control circuit 24b to release the resonant state of the LC marker 24a in each imaging timing of the imaging unit 21, which is sequentially repeated at a predetermined time interval.

The power supply unit 26 is achieved using a switching circuit, a button-type battery, or the like, and supplies electric power to the aforementioned imaging unit 21, signal processing unit 22, transmitting unit 23, and control unit 25 upon being switched to an on-state by the switching circuit.

Figure 3:
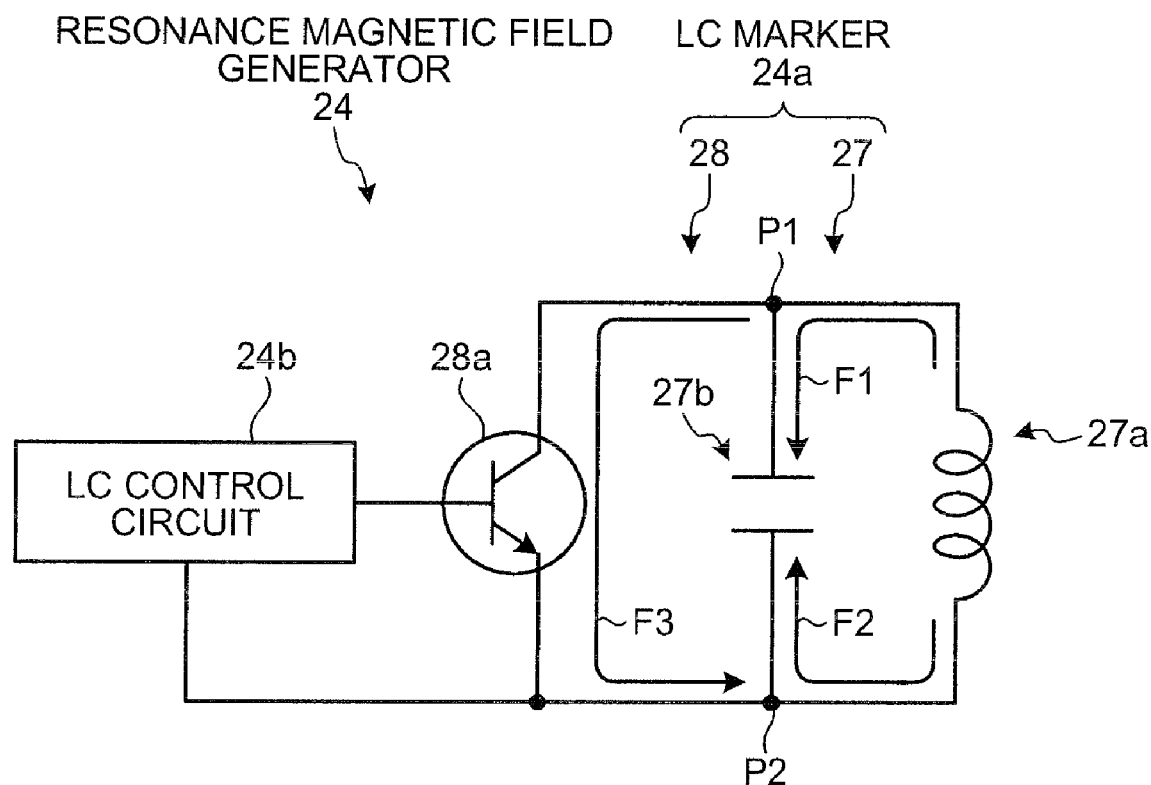
FIG. 3 is a schematic view showing one circuit configuration example of a resonance magnetic field generator of the capsule medical device in accordance with the first embodiment of the present invention.

Next, the resonance magnetic field generator 24 of the capsule medical device 2 will be described in detail. FIG. 3 is a schematic view showing one circuit configuration example of the resonance magnetic field generator of the capsule medical device in accordance with the first embodiment of the present invention. The resonance magnetic field generator 24 is provided with the LC marker 24a and the LC control circuit 24b as described above.

More specifically, as shown in FIG. 3, the LC marker 24a is achieved by an LC resonance circuit 27 for resonating with the driving magnetic field of the aforementioned driving magnetic field generator 10 to thereby generate a resonance magnetic field, and a current bypass circuit 28 for forming an alternative path of a current in the LC resonance circuit 27. The LC resonance circuit 27 is achieved by parallel connection of a coil 27a and a capacitor 27b, and has a resonance frequency determined by the coil 27a and the capacitor 27b. If the LC resonance circuit 27 is in the resonant state, it resonates with the driving magnetic field of the driving magnetic field generator 10 to generate a resonance magnetic field, and emits the resonance magnetic field to the aforementioned three-dimensional space S. Meanwhile, if the LC resonance circuit 27 is in the non-resonant state, it does not generate the resonance magnetic field even when the driving magnetic field of the driving magnetic field generator 10 is received.

The current bypass circuit 28 is connected to the LC resonance circuit 27 in parallel, and forms the alternative path of the current in the LC resonance circuit 27. Specifically, the current bypass circuit 28 has a switching element 28a such as a transistor or the like, and it is achieved by parallel connection of the switching element 28a and LC resonance circuit 27. In this case, one terminal of the switching element 28a (for example, collector) is connected to a point of contact P1 between terminals of the coil 27a and the capacitor 27b, and the other terminal of the switching element 28a (for example, emitter) is connected to a point of contact P2 between terminals of the coil 27a and the capacitor 27b. The current bypass circuit 28 switches an on-off state of the switching element 28a based on control of the LC control circuit 24b, and when the switching element 28a is an on-state, it diverts the current in the LC resonance circuit 27 to release the resonant state of the LC resonance circuit 27, whereas when the switching element 28a is an off-state, it alternates the current between the coil 27a and the capacitor 27b to set the LC resonance circuit 27 to the resonant state.

The LC control circuit 24b functions as a resonance control circuit for controlling a current flow through the current bypass circuit 28 to thereby switch the resonant state and the non-resonant state of the LC resonance circuit 27. Specifically, the LC control circuit 24b is connected to the current bypass circuit 28 as shown in FIG. 3, and controls the current flow through the current bypass circuit 28, namely, whether or not to divert the current in the LC resonance circuit 27 to the current bypass circuit 28 by a base current inputted into the switching element 28a of the current bypass circuit 28. The LC control circuit 24b switches the resonant state and the non-resonant state of the LC resonance circuit 27 through the control of the current flow through the current bypass circuit 28.

Here, the LC control circuit 24b applies a predetermined base current to the switching element 28a at the timing (imaging timing of the imaging unit 21) instructed by the aforementioned control unit 25 of the capsule medical device 2, and maintains a state of applying this base current during the predetermined period. As a result, the switching element 28a is in an on-state during a predetermined period from this imaging timing, and the current bypass circuit 28 is in a state of allowing the current in the LC resonance circuit 27 to be made to flow. In this case, the LC resonance circuit 27 is in a state of relieving the resonant state (non-resonant state) during this predetermined period. Namely, when the coil 27a generates a current in response to the driving magnetic field of the driving magnetic field generator 10, a current from the one end (point of contact P1 side) of the coil 27a reaches the point of contact P2 through an alternative path F3 formed of the current bypass circuit 28 without reaching the capacitor 27b, after passing through the point of contact P1. Meanwhile, a current from the other end (point of contact P2 side) of the coil 27a passes through the point of contact P2, and reaches the capacitor 27b (refer to a path F2 shown in FIG. 3). The LC resonance circuit 27 in the non-resonant state does not generate the resonance magnetic field even when it receives the driving magnetic field of the driving magnetic field generator 10.

Meanwhile, the LC control circuit 24b does not apply the base current to the switching element 28a of the current bypass circuit 28 during a normal period excluding the aforementioned imaging timing of the imaging unit 21 and a predetermined period from the imaging timing thereof. As a result, the switching element 28a is in an off-state during this normal period, and the current bypass circuit 28 is in a state of not allowing the current in the LC resonance circuit 27 to be made to flow. In this case, the LC resonance circuit 27 is in a state of allowing the resonance magnetic field to be generated, namely, in the resonant state during this normal period. In the LC resonance circuit 27 of the resonant state, when the coil 27a generates the current in response to the driving magnetic field of the driving magnetic field generator 10, the current from the one end (point of contact P1 side) of the coil 27a reaches the capacitor 27b not passing through the alternative path F3 formed of the aforementioned current bypass circuit 28, but passing through a path F1 in the LC resonance circuit 27, and the current from the other end (point of contact P2 side) of the coil 27a reaches the capacitor 27b through the path F2 in the LC resonance circuit 27. The LC resonance circuit 27 in the resonant state resonates with the driving magnetic field of the driving magnetic field generator 10 to thereby generate the resonance magnetic field.

Incidentally, it is desirable that a frequency of the driving magnetic field of the driving magnetic field generator 10 applied to the resonance magnetic field generator 24 may be substantially the same as the resonance frequency of the LC resonance circuit 27 specified by the coil 27a and the capacitor 27b.

Figure 4:
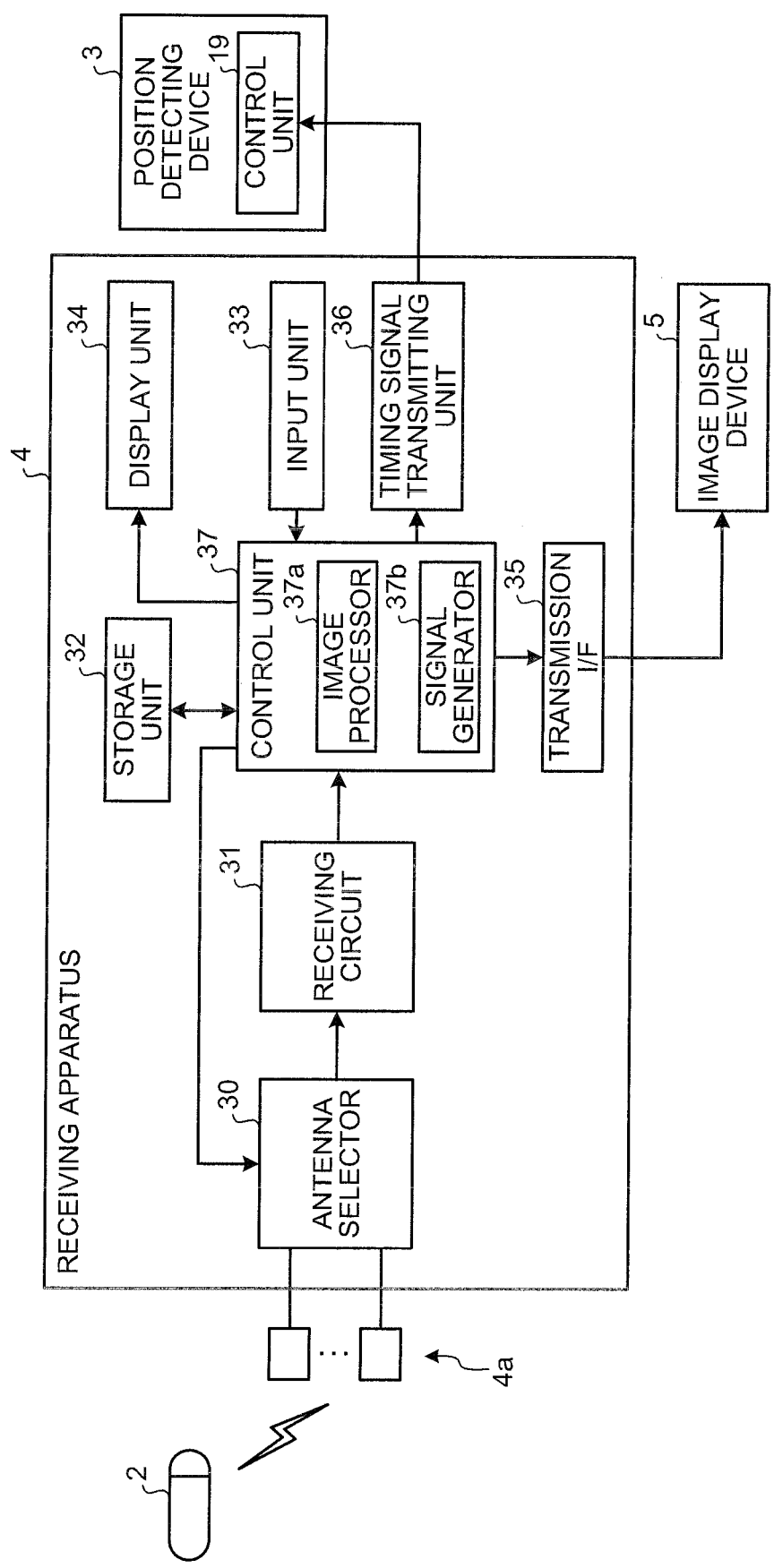
FIG. 4 is a block diagram schematically showing one configuration example of a receiving apparatus of the position detecting system in accordance with the first embodiment of the present invention.

Next, the receiving apparatus 4 of the position detecting system 1 in accordance with the first embodiment of the present invention will be described in detail. FIG. 4 is a block diagram schematically showing one configuration example of the receiving apparatus of the position detecting system in accordance with the first embodiment of the present invention. As shown in FIG. 4, the receiving apparatus 4 of the position detecting system 1 in accordance with the first embodiment is provided with the aforementioned plurality of receiving antennas 4a, an antenna selector 30 for selecting a receiving antenna suitable for reception of a radio signal among the plurality of receiving antennas 4a, and a receiving circuit 31 for receiving the image signal of the subject via the plurality of receiving antennas 4a. In addition, the receiving apparatus 4 is provided with a storage unit 32 for storing information including a set of images in the body of the subject and the like, an input unit 33 for inputting a variety of information, a display unit 34 for displaying a variety of information, such as the image in the body of the subject and the like, a transmission interface (hereinafter, referred to as the "transmission I/F") 35 for transmitting the image signal of the subject to the aforementioned image display device 5, a timing signal transmitting unit 36 for transmitting a predetermined timing signal to the control unit 19 of the position detecting device 3, and a control unit 37 for controlling each component unit of the receiving apparatus 4.

The antenna selector 30 selects a receiving antenna suitable for wireless communication with the capsule medical device 2 among the plurality of receiving antennas 4a. Specifically, the antenna selector 30 selects a receiving antenna with the highest received field intensity among the plurality of receiving antennas 4a based on control of the control unit 37, and connects the selected receiving antenna to the receiving circuit 31. The antenna selector 30 transmits to the receiving circuit 31 a radio signal from the capsule medical device 2, which is captured by the selected receiving antenna.

The receiving circuit 31 receives the image signal from the capsule medical device 2 via the receiving antenna selected by the antenna selector 30 among the plurality of receiving antennas 4a. In this case, the receiving circuit 31 receives from the antenna selector 30 the radio signal from the capsule medical device 2, performs predetermined demodulation processing and the like on the received radio signal to thereby extract the image signal included in the radio signal. The image signal extracted by the receiving circuit 31 is the image signal wirelessly transmitted by the capsule medical device 2, and includes the image in the body of the subject captured by the imaging unit 21 of the capsule medical device 2, the synchronizing signal, and the like. The receiving circuit 31 transmits to the control unit 37 the image signal from the capsule medical device 2.

The storage unit 32 stores a variety of information instructed to be stored by the control unit 37, and sends out to the control unit 37 information instructed to be read by the control unit 37 among the stored variety of information. A variety of information stored by the storage unit 32 includes, for example, a set of images in the body of the subject captured by the capsule medical device 2, information inputted by the input unit 33, and the like. It is to be noted that the storage unit 32 may be various storage media, such as a RAM, an EEPROM, a flash memory, or a hard disk, which rewritably store information, or may be portable recording media removably attached to the receiving apparatus 4.

The input unit 33 is achieved using an input device, such as an input button or the like, and inputs a variety of information into the control unit 37 according to an input operation. The variety of information inputted by the input unit include, for example, instruction information instructed to the control unit 37, patient information on the subject which introduces the capsule medical device 2 into the inside of the body thereof, examination information, and the like.

The display unit 34 is achieved using various displays, such as a liquid crystal display or the like, and displays a variety of information instructed to be displayed by the control unit 37. The variety of information displayed by the display unit 34 include, for example, the image in the body of the subject captured by the capsule medical device 2, the patient information and examination information of the subject, and the like.

The transmission I/F 35 sequentially transmits to the image display device 5 the image signal of the subject instructed to be transmitted by the control unit 37 (refer to FIG. 1). It is to be noted that the transmission I/F 35 may sequentially transmit the image signal of the subject to the image display device 5 through wireless communication, or may sequentially transmit the image signal of the subject to the image display device 5 through cable communication via a cable or the like.

The timing signal transmitting unit 36 transmits a timing signal for notifying a timing when the capsule medical device 2 in the three-dimensional space S is in the non-resonant state (namely, timing when the aforementioned resonant state of the LC resonance circuit 27 is released) to the control unit 19 of the position detecting device 3. The timing signal transmitting unit 36 transmits the timing signal at substantially the same timing as the timing when the resonant state of the LC resonance circuit 27 (refer to FIG. 3) is released, based on the control of the control unit 37. As a result, the timing signal transmitting unit 36 notifies the control unit 19 of the position detecting device 3 that the capsule medical device 2 in the three-dimensional space S is in the non-resonant state.

The control unit 37 controls each component unit (the antenna selector 30, the receiving circuit 31, the storage unit 32, the input unit 33, the display unit 34, the transmission I/F 35, and the timing signal transmitting unit 36) of the receiving apparatus 4, and controls input and output of signals between respective component units. Specifically, the control unit 37 controls each operation of the aforementioned storage unit 32 and display unit 34 based on instruction information inputted by the input unit 33, and controls operation start and operation completion of the antenna selector 30 and the receiving circuit 31. In addition, the control unit 37 controls an operation of switching the receiving antennas by the antenna selector 30, based on signal strength of the image signal acquired from the receiving circuit 31 to thereby cause the antenna selector 30 to select the receiving antenna with the highest received field intensity among the plurality of receiving antennas 4a.

In addition, the control unit 37 has an image processor 37a for generating the image in the body of the subject, and a signal generator 37b for generating the timing signal. The image processor 37a acquires the image signal extracted by the receiving circuit 31, and generates image data based on the acquired image signal, namely the image in the body of the subject captured by the capsule medical device 2 at each time of acquiring the image signal. The control unit 37 causes the storage unit 32 to sequentially store therein the image in the body of the subject generated by the image processor 37a, and also causes the display unit 34 to sequentially displays the image in the body of the subject.

The signal generator 37b acquires the image signal extracted by the receiving circuit 31, and generates the aforementioned timing signal at each time of acquiring the image signal. In this case, the signal generator 37b extracts a synchronizing signal (vertical synchronizing signal or horizontal synchronization signal) included in the image signal acquired from the receiving circuit 31, and uses the extracted synchronizing signal as the timing signal. The control unit 37 transmits the obtained timing signal to the timing signal transmitting unit 36 whenever the timing signal is generated by the signal generator 37b, and controls the timing signal transmitting unit 36 to transmit the timing signal to the control unit 19 of the position detecting device 3. As a result, the control unit 37 can cause the timing signal transmitting unit 36 to transmit the timing signal at substantially the same timing as the timing when the resonant state of the aforementioned LC resonance circuit 27 is released.

Figure 5:
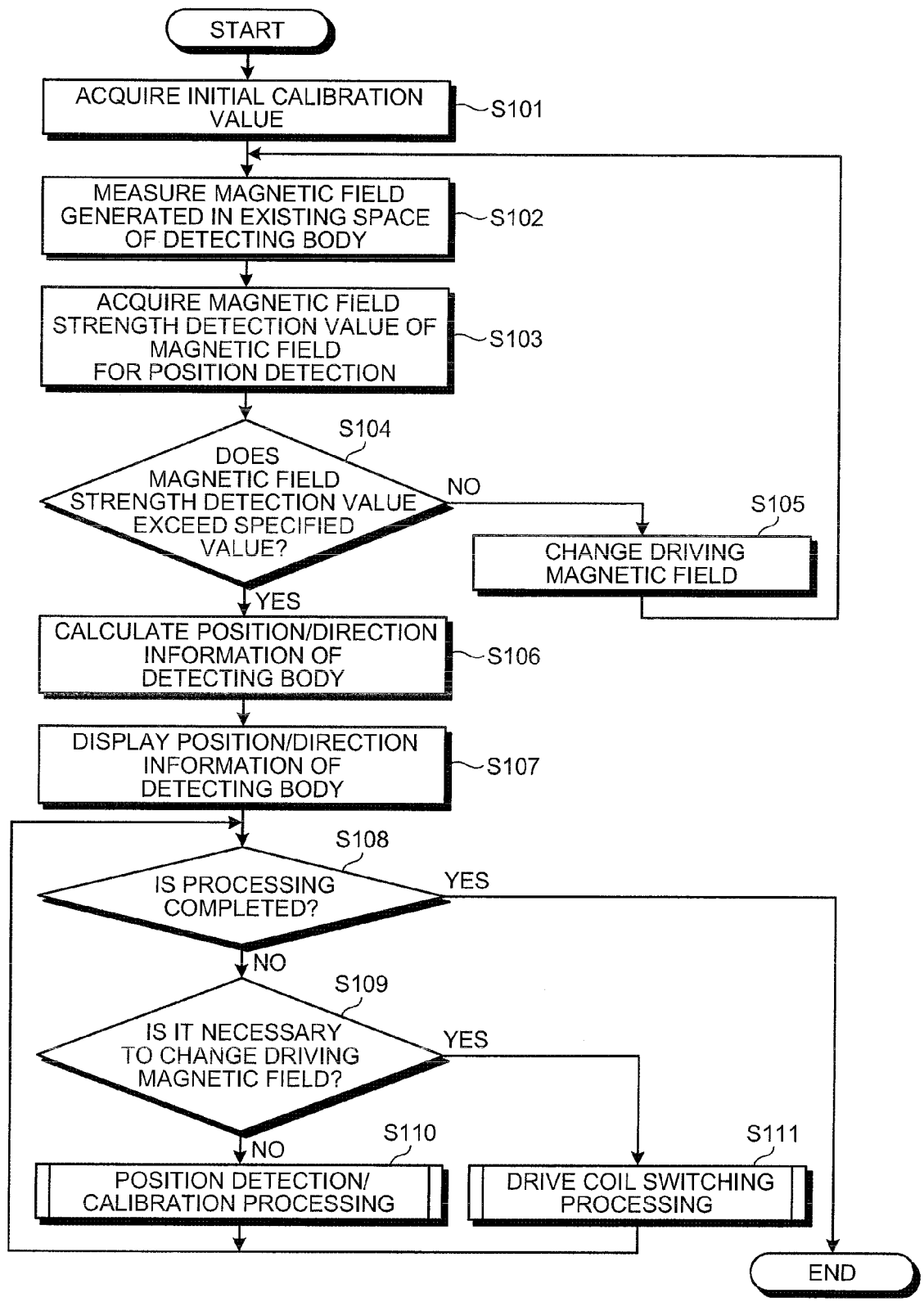
FIG. 5 is a flow chart illustrating a procedure of a position detecting device upon detecting a position and a direction of a detecting body inside three-dimensional space.

Next, an operation of the position detecting system 1 in accordance with the first embodiment of the present invention will be described. FIG. 5 is a flow chart illustrating a procedure of the position detecting device upon detecting the position and direction of the capsule medical device 2 which is the detecting body inside the three-dimensional space S.

As shown in FIG. 5, the control unit 19 of the position detecting device 3 first acquires an initial calibration value on each of the drive coils 10a to 10c of the driving magnetic field generator 10 (Step S101). Specifically, the control unit 19 causes the drive coil 10a to generate the driving magnetic field in the X-axis direction inside the empty three-dimensional space S where the capsule medical device 2 which is the detecting body does not exist. In this case, the magnetic field detector 13 detects the magnetic field generated inside the empty three-dimensional space S, namely, the environmental magnetic field including the driving magnetic field in the X-axis direction. The control unit 19 acquires a magnetic field strength detection value of the environmental magnetic field by the magnetic field detector 13, and sets the acquired magnetic field strength detection value of the environmental magnetic field (namely, environmental magnetic field including the driving magnetic field in the X-axis direction) to an initial X calibration value. The control unit 19 stores the initial X calibration value in the storage unit 18 as the X calibration value 18a. Further, the control unit 19 causes the drive coil 10b to generate the driving magnetic field in the Y-axis direction inside the empty three-dimensional space S. In this case, the magnetic field detector 13 detects the magnetic field generated inside the empty three-dimensional space S, namely, the environmental magnetic field including the driving magnetic field in the Y-axis direction. The control unit 19 acquires a magnetic field strength detection value of the environmental magnetic field by the magnetic field detector 13, and sets the acquired magnetic field strength detection value of the environmental magnetic field (namely, environmental magnetic field including the driving magnetic field in the Y-axis direction) to an initial Y calibration value. The control unit 19 stores the initial Y calibration value in the storage unit 18 as the Y calibration value 18b. Still further, the control unit 19 causes the drive coil 10c to generate the driving magnetic field in the Z-axis direction inside the empty three-dimensional space S. In this case, the magnetic field detector 13 detects the magnetic field generated inside the empty three-dimensional space S, namely, the environmental magnetic field including the driving magnetic field in the Z-axis direction. The control unit 19 acquires a magnetic field strength detection value of the environmental magnetic field by the magnetic field detector 13, and sets the acquired magnetic field strength detection value of the environmental magnetic field (namely, environmental magnetic field including the driving magnetic field in the Z-axis direction) to an initial Z calibration value. The control unit 19 stores the initial Z calibration value in the storage unit 18 as the Z calibration value 18c.

It is to be noted that a sequence of generating the driving magnetic fields by the driving magnetic field generator 10 to the empty three-dimensional space S at Step S101 may be a desired sequence as long as the drive coils 10a to 10c for generating the driving magnetic fields correspond to the calibration values acquired by the control unit 19. Namely, the sequence of generating the driving magnetic fields may be a sequence of the X-axis direction, the Y-axis direction, and the Z-axis direction; a sequence of the X-axis direction, the Z-axis direction, and the Y-axis direction; a sequence of the Y-axis direction, the X-axis direction, and the Z-axis direction; a sequence of the Y-axis direction, the Z-axis direction, and the X-axis direction; a sequence of the Z-axis direction, the X-axis direction, and the Y-axis direction; and a sequence of the Z-axis direction, the Y-axis direction, and the X-axis direction.

After aforementioned Step S101 is completed, the capsule medical device 2 is introduced into the inside of the three-dimensional space S (specifically, inside of the subject), and the control unit 19 measures a magnetic field generated in an existing space of the capsule medical device 2 which is the detecting body, namely, the three-dimensional space S (Step S102). At Step S102, the control unit 19 causes a drive coil selected by the coil selector 19a among the drive coils 10a to 10c to generate the driving magnetic field. In this case, the magnetic field detector 13 detects a spatial magnetic field including the driving magnetic field of the selected drive coil, and the resonance magnetic field from the capsule medical device 2. The control unit 19 acquires a magnetic field strength detection value of the spatial magnetic field by the magnetic field detector 13 as a magnetic field measured value in the three-dimensional space S.

Subsequently, the control unit 19 acquires a magnetic field strength detection value of the magnetic field for position detection of the capsule medical device 2 inside the three-dimensional space S (Step S103). At Step S103, the control unit 19 reads from the storage unit 18 a calibration value corresponding to the drive coil in the driving state among the drive coils 10a to 10c. For example, if the drive coil in the driving state at Step S102 is the drive coil 10c, the control unit 19 reads from the storage unit 18 the Z calibration value 18c corresponding to the drive coil 10c in the driving state. The control unit 19 subtracts the read calibration value from the magnetic field strength detection value of the spatial magnetic field acquired at aforementioned Step S102, and calculates a magnetic field strength detection value of the resonance magnetic field from the capsule medical device 2, which is the magnetic field for position detection.

Next, the control unit 19 determines whether or not the magnetic field strength detection value of the resonance magnetic field acquired (calculated) at Step S103 exceeds a predetermined specified value (Step S104), and if the magnetic field strength detection value of the resonance magnetic field is the specified value or less (Step S104, No), it changes the driving magnetic field actually generated in the three-dimensional space S (Step S105). Subsequently, the control unit 19 returns to aforementioned Step S102, and repeats the procedure after Step S102.

At Steps S104 and S105, the coil selector 19a compares the magnetic field strength detection value of the resonance magnetic field with the specified value previously set, and if the magnetic field strength detection value of the resonance magnetic field is the specified value or less (namely, if the magnetic field strength detection value of the resonance magnetic field is weak as the magnetic field for position detection), it selects a drive coil other than a drive coil actually in the driving state among the drive coils 10a to 10c. For example, if the drive coil actually in the driving state is the drive coil 10c, the coil selector 19a selects a drive coil other than the drive coil 10c, namely the drive coil 10a or the drive coil 10b.

The control unit 19 controls the coil switching unit 12 to switch from the drive coil actually in the driving state to other drive coil selected by the coil selector 19a to thereby change the driving magnetic field in the three-dimensional space S.

Meanwhile, if the magnetic field strength detection value of the resonance magnetic field exceeds the specified value at Step S104 (Step S104, Yes), the control unit 19 determines that the magnetic field strength detection value of the resonance magnetic field is a sufficient value as the magnetic field for position detection, and calculates position/direction information of the detecting body based on the magnetic field strength detection value of the resonance magnetic field (Step S106).

At Step S106, the control unit 19 transmits the magnetic field strength detection value of the spatial magnetic field by the magnetic field detector 13, and the calibration value corresponding to the drive coil in the driving state to the position/direction calculating unit 15, and controls the position/direction calculating unit 15 to calculate the position/direction information of the detecting body based on the transmitted magnetic field strength detection value and calibration value. In this case, the position/direction calculating unit 15 subtracts the calibration value from the magnetic field strength detection value of the spatial magnetic field acquired from the control unit 19 to calculate the magnetic field strength detection value of the resonance magnetic field from the capsule medical device 2, and calculates a position and a direction inside the three-dimensional space S of the capsule medical device 2 which is the detecting body based on the calculated magnetic field strength detection value of the resonance magnetic field. The control unit 19 acquires the calculation result of the position and the direction by the position/direction calculating unit 15 as the position/direction information of the capsule medical device 2 inside the three-dimensional space S.

For example, if the drive coil in the driving state is the drive coil 10a, the control unit 19 transmits to the position/direction calculating unit 15 the magnetic field strength detection value of the spatial magnetic field acquired by the magnetic field detector 13, and the X calibration value 18a corresponding to the drive coil 10a. The position/direction calculating unit 15 subtracts the X calibration value 18a from this magnetic field strength detection value of the spatial magnetic field to calculate the magnetic field strength detection value of the resonance magnetic field, and calculates the position/direction information of the capsule medical device 2 inside the three-dimensional space S based on the calculated magnetic field strength detection value of the resonance magnetic field.

The control unit 19 displays on the display unit 17 the position/direction information of the detecting body calculated at Step S106 after executing aforementioned Step S106 (Step S107). At Step S107, the control unit 19 displays on the display unit 17 the current position/direction information of the capsule medical device 2 which is the detecting body inside the three-dimensional space S to thereby update the display information on the display unit 17 (position/direction information of the capsule medical device 2, track information of the capsule medical device 2, and the like) to the up-to-date information.

Subsequently, the control unit 19 determines whether or not the processing is complete (Step S108), and if the processing is completed (Step S108, Yes), it completes the present processing. At Step S108, the control unit 19 determines the processing is completed if instruction information for instructing the processing completion is inputted by the input unit 16.

Meanwhile, if it is not the processing completion at Step S108 (Step S108, No), the control unit 19 determines whether or not it is necessary to change the driving magnetic field in the three-dimensional space S (Step S109). At Step S109, the control unit 19 performs a similar procedure to that at aforementioned Steps S102 through S104, and if the magnetic field strength detection value of the resonance magnetic field thus obtained is less than the predetermined specified value, it determines that the driving magnetic field needs to be changed, whereas if the magnetic field strength detection value of the resonance magnetic field exceeds the predetermined specified value, it determines that the driving magnetic field needs not to be changed.

If the control unit 19 determines that the driving magnetic field needs not to be changed at Step S109 (Step S109, No), it executes the position detection/calibration processing for processing the position/direction information of the capsule medical device 2 inside the three-dimensional space S, or the calibration value (Step S110), and subsequently it returns to aforementioned Step S108, and repeats the procedure after Step S108. Meanwhile, if the control unit 19 determines that the driving magnetic field needs to be changed at Step S109 (Step S109, Yes), it executes the drive coil switching processing for switching the drive coil that generates the driving magnetic field in the three-dimensional space S (Step S111), and subsequently it returns to aforementioned Step S108, and repeats the procedure after Step S108.

Figure 6:
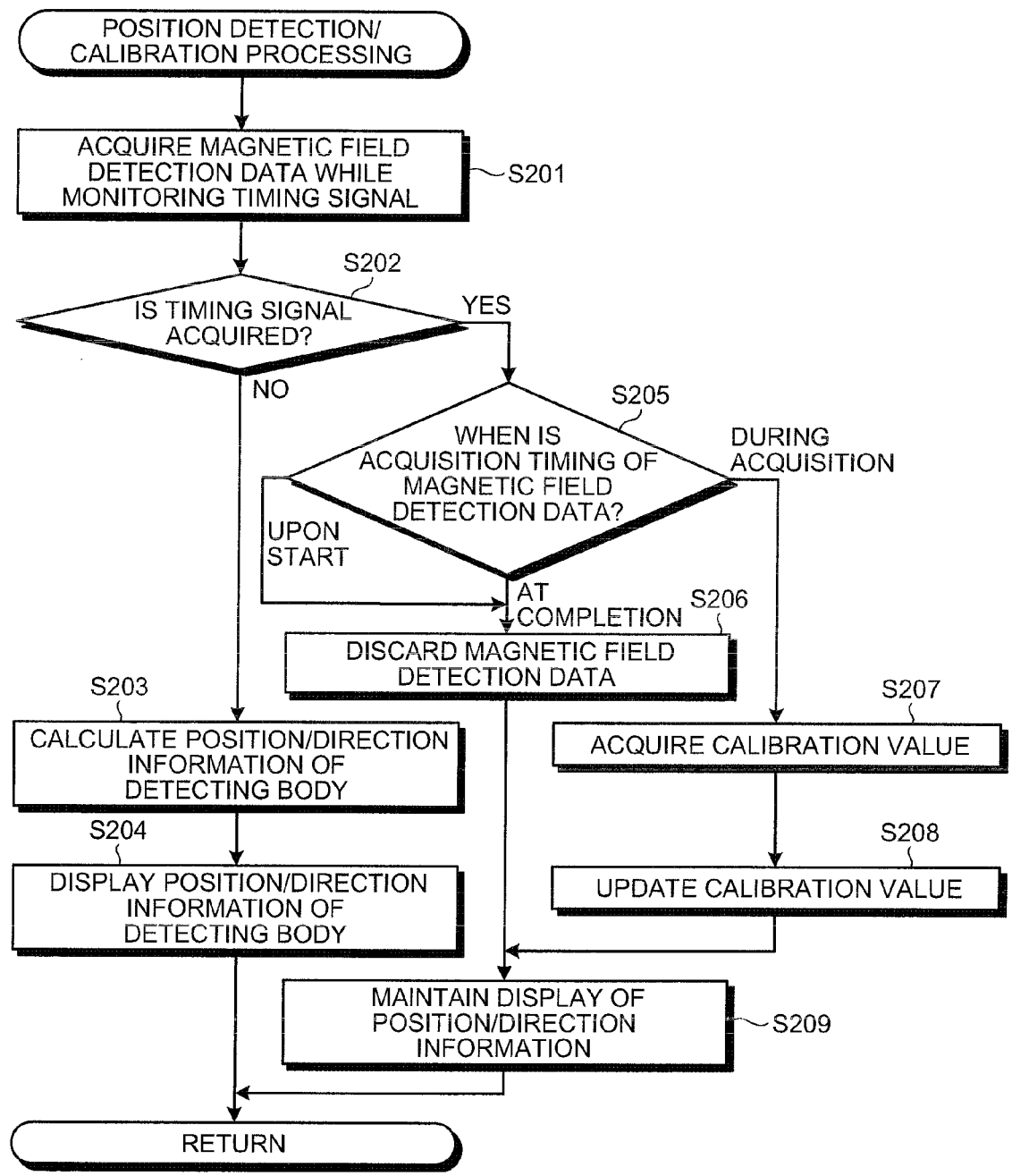
FIG. 6 is a flow chart illustrating a procedure of position detection/calibration processing of the position detecting system in accordance with the first embodiment of the present invention.

Next, the position detection/calibration processing at aforementioned Step S110 will be described in detail. FIG. 6 is a flow chart illustrating a procedure of position detection/calibration processing of the position detecting system in accordance with the first embodiment of the present invention.

In the position detection/calibration processing at aforementioned Step S110, the control unit 19 of the position detecting device 3 first acquires the magnetic field detection data of the magnetic field detector 13 while monitoring the timing signal from the receiving apparatus 4 as shown in FIG. 6 (Step S201). At Step S201, the control unit 19 acquires only the magnetic field detection data of the magnetic field detector 13 via the receiving unit 14, or acquires the magnetic field detection data and the timing signal from the receiving apparatus 4.

Next, the control unit 19 determines whether or not the timing signal from the receiving apparatus 4 is acquired as well as the magnetic field detection data of the magnetic field detector 13 at aforementioned Step S201 (Step S202). Here, the magnetic field detection data of the magnetic field detector 13 is the magnetic field strength detection value of the spatial magnetic field inside the three-dimensional space S including the resonance magnetic field from the capsule medical device 2 and the environmental magnetic field, if it is the data acquired at a period different from that of the timing signal from the receiving apparatus 4, whereas it is a practical magnetic field strength detection value of the environmental magnetic field in the three-dimensional space S, if it is the data acquired at the same period as that of the timing signal from the receiving apparatus 4. If the timing signal from the receiving apparatus 4 is not acquired at the acquisition timing of the magnetic field detection data (Step S202, No), the control unit 19 calculates the position/direction information of the detecting body using the magnetic field detection data (Step S203).

At Step S203, the data controller 19b employs the magnetic field detection data acquired by the control unit 19 at a period different from that of the timing signal from the receiving apparatus 4, namely, the magnetic field strength detection value of the spatial magnetic field inside the three-dimensional space S, including the resonance magnetic field from the capsule medical device 2 and the environmental magnetic field, as operation data of the position/direction calculating unit 15. The control unit 19 transmits to the position/direction calculating unit 15 the magnetic field strength detection value of the spatial magnetic field employed by the data controller 19b and the calibration value corresponding to the drive coil in the driving state, and controls the position/direction calculating unit 15 to calculate the position and the direction of the capsule medical device 2 which is the detecting body inside the three-dimensional space S, based on the transmitted magnetic field strength detection value and calibration value. The control unit 19 acquires the calculation result of the position and the direction by the position/direction calculating unit 15 as the position/direction information of the capsule medical device 2 inside the three-dimensional space S.

Subsequently, the control unit 19 displays on the display unit 17 the position/direction information of the detecting body acquired at Step S203 (Step S204) to then return to aforementioned Step S110. At Step S204, the control unit 19 displays on the display unit 17 the current position/direction information of the capsule medical device 2 which is the detecting body inside the three-dimensional space S to thereby update the display information on the display unit 17 (including the position/direction information of the capsule medical device 2, the track information of the capsule medical device 2, and the like) to the up-to-date information.

Meanwhile, if the control unit 19 acquires the timing signal from the receiving apparatus 4 as well as the magnetic field detection data of the magnetic field detector 13 at aforementioned Step S201 (Step S202, Yes), it determines the acquisition timing of the magnetic field detection data (Step S205). Here, the acquisition timing of the magnetic field detection data includes a timing when the control unit 19 starts acquiring the timing signal from the receiving apparatus 4, a timing when the control unit 19 completes acquiring the timing signal from the receiving apparatus 4, and a timing between the acquisition start timing and the acquisition completion timing.

If the acquisition timing of the magnetic field detection data is the acquisition start timing of the timing signal (Step S205, upon start), or if it is the acquisition completion timing of the timing signal (Step S205, upon completion), the control unit 19 discards the magnetic field detection data (Step S206). At Steps S205 and S206, the data controller 19b confirms that the acquisition timing of the magnetic field detection data is substantially coincident with the acquisition start timing or acquisition completion timing of the timing signal, and discards the magnetic field detection data acquired at the acquisition start timing or acquisition completion timing of the timing signal. The control unit 19 forbids the position/direction calculating processing of the position/direction calculating unit 15 at the acquisition start timing of the timing signal by discarding the magnetic field detection data in this way.

Subsequently, the control unit 19 maintains the display of the position/direction information of the capsule medical device 2 by the display unit 17 (Step S209), after which it returns to aforementioned Step S110. Here, the control unit 19 displays on the display unit 17 the last position/direction information among the pieces of position/direction information of the capsule medical device 2 calculated by the position/direction calculating unit 15 up to this time, and the control unit 19 maintains the display state of the display unit 17 at Step S209.

Meanwhile, if the acquisition timing of the magnetic field detection data is the timing between the acquisition start timing and the acquisition completion timing of the timing signal (Step S205, during acquisition), the control unit 19 acquires the calibration value based on the magnetic field detection data (Step S207).

At Steps S205 and S207, the data controller 19b confirms that the acquisition timing of the magnetic field detection data is substantially coincident with the timing between the acquisition start timing and the acquisition completion timing of the timing signal (namely, timing during acquisition of the timing signal). Here, the magnetic field detection data acquired by the control unit 19 at the timing during acquisition of the timing signal is the magnetic field detection data of the magnetic field detector 13 when the capsule medical device 2 is in the non-resonant state, namely, the practical magnetic field detection data of the environmental magnetic field inside the three-dimensional space S. The data controller 19b employs the magnetic field strength detection value of the environmental magnetic field, which is the magnetic field detection data at the timing during acquisition of the timing signal, as the up-to-date calibration value. In this case, the control unit 19 acquires the employed calibration value as the up-to-date calibration value corresponding to the drive coil actually in the driving state (any one of the drive coils 10a to 10c). It is to be noted that the control unit 19 forbids the position/direction calculating processing of the position/direction calculating unit 15 at the timing of acquiring the magnetic field detection data as the calibration value in this way, namely, at the timing during acquisition of the timing signal.

Subsequently, the control unit 19 performs update processing of the calibration value acquired at Step S207 (Step S208), and proceeds to aforementioned Step S209 after executing Step S208. After executing Step S209, the control unit 19 then returns to aforementioned Step S110. At Step S208, the control unit 19 stores (overwrite) the calibration value acquired at Step S207 in the storage unit 18 as the up-to-date information of the calibration value corresponding to the drive coil actually in the driving state to thereby update the calibration value to the up-to-date value.

Figure 7:
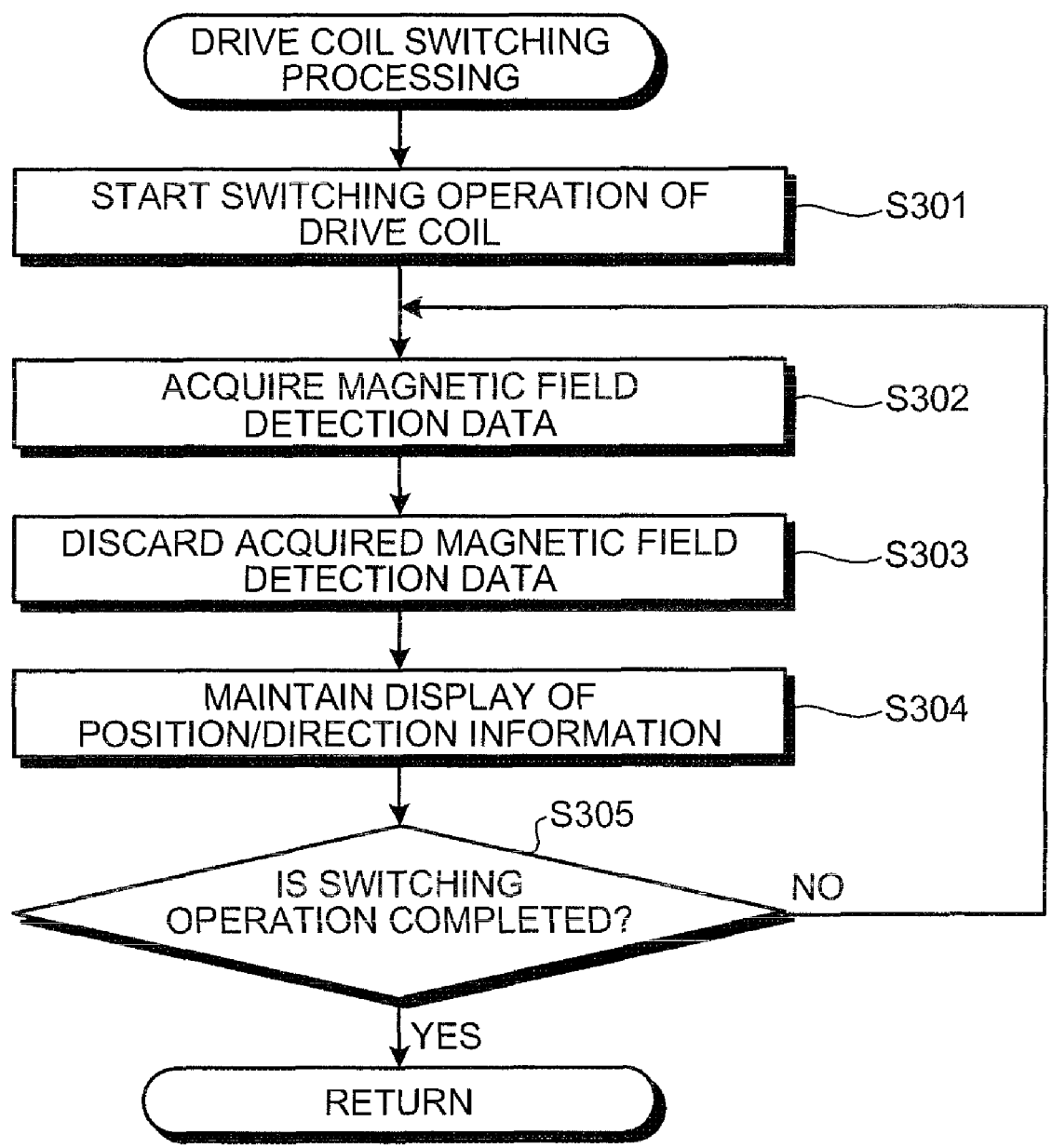
FIG. 7 is a flow chart illustrating a procedure of drive coil switching processing of the position detecting system in accordance with the first embodiment of the present invention.

Next, the drive coil switching processing at aforementioned Step S111 will be described in detail. FIG. 7 is a flow chart illustrating a procedure of the drive coil switching processing of the position detecting system in accordance with the first embodiment of the present invention.

In the drive coil switching processing at aforementioned Step S111, the control unit 19 of the position detecting device 3 first causes the coil switching unit 12 to start switching operation of the drive coils 10a to 10c as shown in FIG. 7 (Step S301). At Step S301, the coil selector 19a selects a coil other than the drive coil actually in the driving state among the drive coils 10a to 10c. Specifically, if the drive coil 10a is actually in the driving state, the coil selector 19a selects either of the drive coils 10a and 10c; if the drive coil 10b is actually in the driving state, it selects either of the drive coils 10a and 10c; and if the drive coil 10c is actually in the driving state, it selects either of the drive coils 10a and 10b. The control unit 19 causes the coil switching unit 12 to start the switching operation to the drive coil selected by the coil selector 19a. The coil switching unit 12 starts the switching operation to switch the drive coil actually in the driving state to the selected drive coil based on the control of the control unit 19.

Next, the control unit 19 acquires magnetic field detection data of the magnetic field detector 13 via the receiving unit 14 (Step S302), and discards the acquired magnetic field detection data (Step S303). At Step S303, the data controller 19b discards all the magnetic field detection data acquired at Step S302, irrespective of the acquisition timing of the magnetic field detection data. As a result, the control unit 19 forbids the position/direction calculating processing of the position/direction calculating unit 15 upon execution of the drive coil switching processing.

It is to be noted that the acquisition timing of the magnetic field detection data at Step S302 includes, for example, an acquisition start timing of the timing signal, an acquisition completion timing of the timing signal, a timing during acquisition of the timing signal, a timing not acquiring the timing signal, and the like.

Subsequently, the control unit 19 maintains the display of the position/direction information of the capsule medical device 2 by the display unit 17 (Step S304). Here, the control unit 19 displays on the display unit 17 the last position/direction information among the pieces of position/direction information of the capsule medical device 2 calculated by the position/direction calculating unit 15 up to this time, and the control unit 19 maintains the display state of the display unit 17 at Step S304.

Subsequently, the control unit 19 determines whether or not the switching operation of the drive coil by the coil switching unit 12 is completed (Step S305). If the control unit 19 determines that the switching operation of the drive coil is not completed (Step S305, No), it returns to aforementioned Step S302, and repeats the procedure after Step S302. Meanwhile, if the control unit 19 determines that the switching operation of the drive coil is completed (Step S305, Yes), it returns to aforementioned Step S111. It is to be noted that the control unit 19 determines that the switching operation of the drive coil is completed, if a predetermined time has elapsed after it causes the coil switching unit 12 to start the switching operation of the drive coil.

Figure 8:
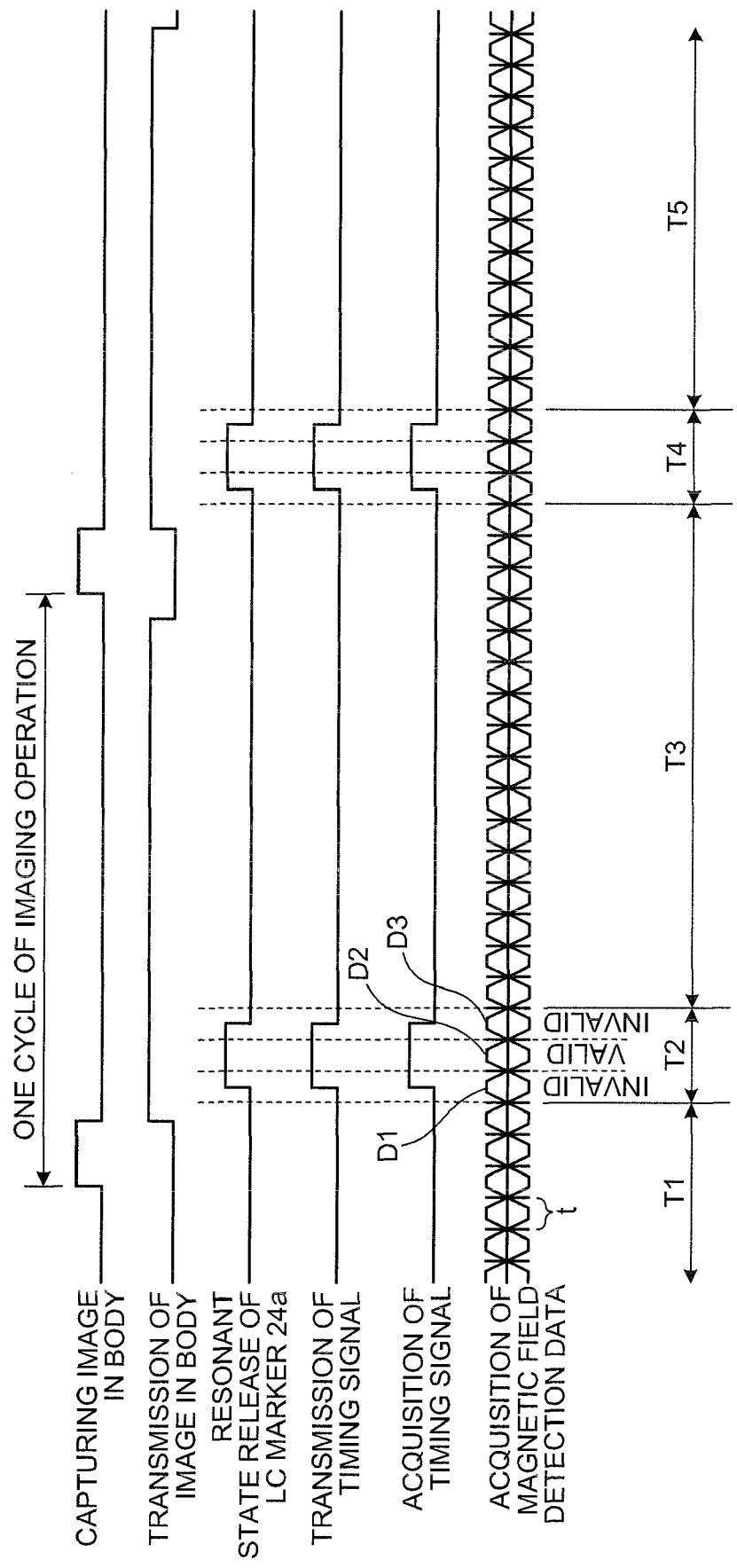
FIG. 8 is a timing chart for concretely explaining an operation of the position detecting system in accordance with the first embodiment of the present invention.

Next, while illustrating one cycle of imaging operation of the image in the body repeatedly executed by the capsule medical device 2 inside the three-dimensional space S (specifically, inside the subject) at a predetermined time interval, the operation of the position detecting system 1 in accordance with the first embodiment of the present invention will be described specifically. FIG. 8 is a timing chart for specifically explaining the operation of the position detecting system in accordance with the first embodiment of the present invention. Incidentally, in FIG. 8, each of timing charts of "capture of image in the body", "transmission of image in the body" and "resonant state release of LC marker 24a" indicates an operation timing of the capsule medical device 2 in the position detecting system 1, and a timing chart of "transmission of timing signal" indicates an operation timing of the receiving apparatus 4 in the position detecting system 1. Additionally, each of timing charts of "acquisition of timing signal" and "acquisition of magnetic field detection data" indicates an operation timing of the control unit 19 of the position detecting device 3 in the position detecting system 1.

The capsule medical device 2 inside the three-dimensional space S captures the image in the body of the subject, and wirelessly transmits the image signal of the captured image in the body to the external receiving apparatus 4 as shown in FIG. 8. In the capsule medical device 2, the LC control circuit 24b releases the resonant state of the LC marker 24a at a timing delayed by a predetermined time from capturing the image in the body (in particular, image capture completion timing) notified by the control unit 25. The LC control circuit 24b maintains a state where the resonant state of the LC marker 24a is released (namely, non-resonant state of the LC marker 24a) during a predetermined period. In this case, the LC control circuit 24b maintains the non-resonant state of the LC marker 24a during a period more than twice the acquisition period (it is a unit time t which will be hereinafter described) of the magnetic field detection data by the control unit 19. As a result, the control unit 19 of the position detecting device 3 will be able to reliably acquire one or more magnetic field detection data of the environmental magnetic field inside the three-dimensional space S within a period when the LC marker 24a is in the non-resonant state.

Here, by delaying the timing of resonant state release of the LC marker 24a from the image capture completion timing by a predetermined time, the position detecting system 1 can substantially synchronize (substantially match) the timing of resonant state release of the LC marker 24a, a timing for the receiving apparatus 4 to transmit the timing signal, and a timing for the control unit 19 of the position detecting device 3 to acquire the timing signal from the receiving apparatus 4 with each other.

Meanwhile, the receiving apparatus 4 receives the image signal of the subject wirelessly transmitted by the capsule medical device 2 via the plurality of receiving antennas 4a. In the receiving apparatus 4, the timing signal transmitting unit 36 starts transmission of timing signal which is the synchronizing signal of the image signal at substantially the same timing as the timing when the resonant state of the LC marker 24a of the capsule medical device 2 is released, as shown in FIG. 8. The receiving apparatus 4 transmits the timing signal to the control unit 19 of the position detecting device 3 during substantially the same period as the period while the resonant state of the aforementioned LC marker 24a is released.

Meanwhile, the position detecting device 3 successively detects the magnetic field in the three-dimensional space S by the magnetic field detector 13, while suitably switching the drive coil in the driving state among the drive coils 10a to 10c of the driving magnetic field generator 10. In the position detecting device 3, the control unit 19 sequentially acquires the magnetic field detection data of the magnetic field detector 13 for every unit time t specified by a predetermined clock frequency, while monitoring the timing signal from the receiving apparatus 4, as shown in FIG. 8.

Here, the control unit 19 sequentially acquires the magnetic field detection data of the magnetic field detector 13 as well as the timing signal from the receiving apparatus 4 at the timing when the resonant state of the LC marker 24a is released. Specifically, the control unit 19 sequentially acquires three pieces of magnetic field detection data D1, D2, and D3 during a period T2 from the acquisition start timing to the acquisition completion timing of the timing signal. In this case, the data controller 19b discards the magnetic field detection data D1 at the acquisition start timing of the timing signal, and the magnetic field detection data D3 (for example, magnetic field detection data next-but-one to the magnetic field detection data D1) at the acquisition completion timing of the timing signal to invalidate the data. Meanwhile, the data controller 19b employs the magnetic field detection data D2 (for example, magnetic field detection data next to the magnetic field detection data D1) at a timing between the acquisition start timing and the acquisition completion timing of the timing signal as valid data.

The control unit 19 acquires the valid magnetic field detection data D2 (namely, magnetic field strength detection value of the environmental magnetic field which is the magnetic field inside the three-dimensional space S excluding the resonance magnetic field from the capsule medical device 2) during the period T2, and overwrites the magnetic field detection data D2 thus acquired on the storage unit 18 as a calibration value corresponding to the drive coil actually in the driving state. Specifically, the control unit 19 overwrites the magnetic field detection data D2 on the storage unit 18 as the X calibration value 18a corresponding to the drive coil 10a, if the drive coil 10*a* is in the driving state, overwrites the magnetic field detection data D2 on the storage unit 18 as the Y calibration value 18*b* corresponding to the drive coil 10*b* if the drive coil 10*b* is in the driving state, and overwrites the magnetic field detection data D2 on the storage unit 18 as the Z calibration value 18*c* corresponding to the drive coil 10*c* if the drive coil 10*c* is in the driving state. Thus, the control unit 19 achieves the update processing of the calibration value corresponding to the drive coil in the driving state. It is to be noted that the control unit 19 forbids the position/direction calculating processing of the position/direction calculating unit 15 during the period T2 for executing the update processing of the calibration value.

Meanwhile, the control unit 19 sequentially acquires the magnetic field detection data of the magnetic field detector 13 for every unit time t during the periods T1 and T3 when the LC marker 24*a* is in the resonant state. Here, the magnetic field detection data of the magnetic field detector 13 during the periods T1 and T3 is a detection data of the spatial magnetic field inside the three-dimensional space S (specifically, magnetic field strength detection value), including the resonance magnetic field from the capsule medical device 2 and the environmental magnetic field. The data controller 19*b* employs the magnetic field detection data during the periods T1 and T3 as the valid data for the position/direction calculating processing of the position/direction calculating unit 15. The control unit 19 transmits to the position/direction calculating unit 15 the magnetic field strength detection value of the spatial magnetic field which is the magnetic field detection data during the periods T1 and T3, and the calibration value corresponding to the drive coil actually in the driving state, and causes the position/direction calculating unit 15 to execute the position/direction calculating processing using the transmitted magnetic field strength detection value and calibration value.

It is to be noted that the control unit 19 causes the position/direction calculating unit 15 to execute the position/direction calculating processing using the X calibration value corresponding to the drive coil 10*a*, and the magnetic field strength detection value of the spatial magnetic field, if the drive coil 10*a* is in the driving state; causes the position/direction calculating unit 15 to execute the position/direction calculating processing using the Y calibration value corresponding to this drive coil 10*b*, and the magnetic field strength detection value of the spatial magnetic field, if the drive coil 10*b* is in the driving state; and causes the position/direction calculating unit 15 to execute the position/direction calculating processing using the Z calibration value corresponding to this drive coil 10*c*, and the magnetic field strength detection value of the spatial magnetic field, if the drive coil 10*c* is in the driving state.

The above position detecting system 1 operates in a manner similar to that of the cases of the periods T2 and T3 also during periods after the aforementioned period T3 (periods T4, T5, and the like shown in FIG. 8). Namely, the position detecting system 1 sequentially detects (calculates) the position/direction information of the capsule medical device 2 inside the three-dimensional space S during a period when the capsule medical device 2 is in the resonant state. Moreover, the position detecting system 1 periodically releases the resonant state of the capsule medical device 2, and updates the calibration value of the position/direction calculating processing within the period when the resonant state is released, whenever the capsule medical device 2 captures the image in the body of the subject, for example.

As described above, in the first embodiment of the present invention, there is provided, inside a capsule medical device which is the detecting body, an LC resonance circuit for resonating with a driving magnetic field in a three-dimensional space to generate a resonance magnetic field, a current bypass circuit connected to the LC resonance circuit in parallel to form an alternative path of a current in the LC resonance circuit, and an LC control circuit for controlling the current flow through the current bypass circuit to switch a resonant state and a non-resonant state of the LC resonance circuit, wherein whenever the capsule medical device captures an image in a body of a subject at a predetermined time interval, the LC control circuit controls the current flow through the current bypass circuit to thereby release the resonant state of the LC resonance circuit periodically during a predetermined period. In addition, whenever a receiving apparatus receives an image signal of the image in the body from the capsule medical device, it transmits the image signal to a position detecting device using a synchronizing signal in the image signal as a timing signal, and the position detecting device acquires and updates a reference value (calibration value) of direction calculation processing of the position of the capsule medical device based on magnetic field detection data in the three-dimensional space detected within an acquisition period of the timing signal, and calculates position/direction information of the capsule medical device based on the calibration value and the magnetic field detection data in the three-dimensional space during a period other than the acquisition period of the timing signal. For this reason, practical environmental magnetic field data in the three-dimensional space under existence of the capsule medical device can be detected even in a state where the capsule medical device exists in the three-dimensional space which is a position detection space, thus allowing the calibration value of the position/direction calculating processing to be periodically acquired and updated so as to be a calibration value approximated to actual environmental magnetic field data in the three-dimensional space. As a result, the practical environmental magnetic field in the three-dimensional space can be detected without removing the capsule medical device even after the capsule medical device is introduced into the three-dimensional space, thus allowing position detection accuracy of the capsule medical device to be improved.

Moreover, since the calibration value is acquired and updated periodically at a predetermined time interval, a time interval between an acquisition timing of the calibration value and a detection timing of the magnetic field in the three-dimensional space can be reduced as short as possible to thereby allow effects on the position/direction calculating processing due to temperature drift of the system, and the like to be suppressed, and as a result, the position detection accuracy of the capsule medical device can be improved.

Further, since the synchronizing signal in the image signal of the image in the body sequentially captured by the capsule medical device is used as the timing signal for indicating the timing when the resonant state of the LC resonance circuit inside the capsule medical device is released, it is not necessary to add a new circuit configuration for wirelessly transmitting the timing signal to the outside thereof to the inside of the capsule medical device, thus allowing an increase in the number of components inside the capsule medical device to be suppressed as less as possible, and also allowing reduction in size of the capsule medical device to be promoted.

Moreover, the LC control circuit applies a predetermined current (for example, base current) to the switching element of the current bypass circuit, and the resonant state of the LC resonance circuit is released by making this switching element in an on-state, so that a period when the LC control circuit consumes electric power can be limited only to a period of maintaining the release of the resonant state of the LC resonance circuit, thus allowing the power consumption of the capsule medical device to be suppressed low.

Further, since an electric device, such as a transistor or the like is used as a switching element (namely, switching element for switching the resonant state and the non-resonant state of the LC resonance circuit) of the current bypass circuit, without using a switching arrangement, such as a reed switch or the like, it is possible to further reduce a circuit configuration thereof and also to suppress power consumption.

Moreover, since the current bypass circuit is connected in parallel to the LC resonance circuit, the alternative path of the current in the LC resonance circuit can be formed without inhibiting a resonance magnetic field generating function of the LC resonance circuit due to an increase in resistance value of the LC resonance circuit or the like.

Next, a modified embodiment of the first embodiment of the present invention will be described. Although there is employed a position detecting system for detecting the position and direction of the capsule medical device 2 that moves the inside of the subject by peristalsis or the like in the aforementioned first embodiment, there is employed a position detecting system for detecting the position and direction of the capsule medical device 2 that is magnetically induced (hereinafter, referred to as the magnetic induction) by an external magnetic field in the modified embodiment of this first embodiment.

Figure 9:
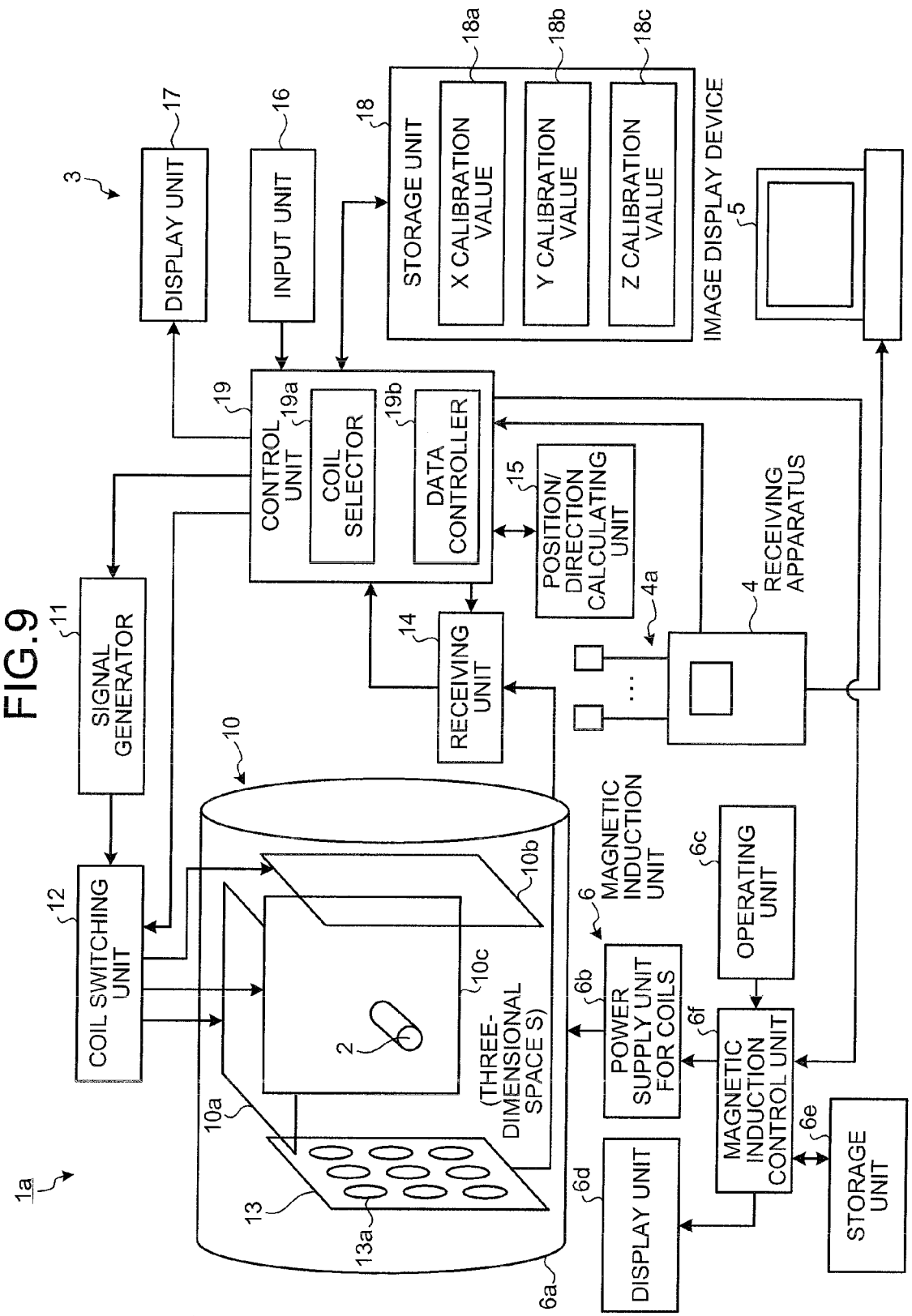
FIG. 9 is a block diagram schematically showing one configuration example of a position detecting system in accordance with a modified embodiment of the first embodiment of the present invention.

FIG. 9 is a block diagram schematically showing one configuration example of the position detecting system in accordance with the modified embodiment of the first embodiment of the present invention. As shown in FIG. 9, a position detecting system 1a in accordance with the modified embodiment of the first embodiment has a configuration in which a magnetic induction unit 6 for magnetically inducing the capsule medical device 2 is added to the position detecting system 1 in accordance with the aforementioned first embodiment. The magnetic induction unit 6 is provided with a magnetic field generator 6a for generating a magnetic field for magnetically inducing the capsule medical device 2, a power supply unit 6b for coil for supplying a current to a coil (electromagnet) of the magnetic field generator 6a, an operating unit 6c for operating magnetic induction of the capsule medical device 2, a display unit 6d for displaying information on the magnetic induction, a storage unit 6e for storing a variety of information, and a magnetic induction controlling unit 6f for controlling each component unit of the magnetic induction unit 6. It is to be noted that in the position detecting system 1a in accordance with the modified embodiment, the capsule medical device 2 is provide with a magnetic substance or an electromagnet (hereinafter, only referred to as the "magnet") which is not particularly shown in the figure, such as a permanent magnet or the like inside the capsule type case, and is magnetically induced by action of the magnetic field generated by the magnetic field generator 6a. Other configurations are the same as those of the first embodiment, and the same reference numeral is given to the same configuration.

The magnetic field generator 6a is achieved by combining a plurality of electromagnets, such as Helmholtz coils or the like, and generates a magnetic field that can induce the capsule medical device 2 inside the three-dimensional space S (detailedly, inside the subject). Specifically, the magnetic field generator 6a generates a magnetic field having a desired strength solely or in combination in each axial direction (the X-axis direction, the Y-axis direction, the Z-axis direction) of the aforementioned absolute coordinate system to thereby form a three-dimensional rotating magnetic field or gradient magnetic field in the absolute coordinate system. The magnetic field generator 6a applies a three-dimensional magnetic field (for example, a rotating magnetic field, a gradient magnetic field, or the like) to the capsule medical device 2 inside the three-dimensional space S (detailedly, inside the subject), and magnetically induces the capsule medical device 2 according to action of the applied three-dimensional magnetic field.

The power supply unit 6b for coil supplies an alternating current required for generation of the aforementioned three-dimensional magnetic field to a plurality of electromagnets (coils) of the driving magnetic field generator 10 based on control of the magnetic induction controlling unit 6f. It is to be noted that the aforementioned three-dimensional magnetic field of the magnetic field generator 6a is controlled by the alternating current (amount of current flow from the power supply unit 6b for coil) supplied from the power supply unit 6b for coil.

The operating unit 6c is achieved using an input device, such as a joystick, an input button, and the like, and inputs operation information of the magnetic induction of the capsule medical device 2 into the magnetic induction controlling unit 6f according to an input operation. It is to be noted that the operation information inputted by the operating unit 6c includes coordinate information for specifying an induction direction of the capsule medical device 2 in the aforementioned absolute coordinate system, speed information of the capsule medical device 2 upon magnetic induction, and the like.

The display unit 6d is achieved using various displays, such as a CRT display, a liquid crystal display, or the like, and displays a variety of information instructed to be displayed by the magnetic induction controlling unit 6f. The display unit 6d displays information useful for the magnetic induction of the capsule medical device 2 inside the three-dimensional space S, for example, a magnetic induction direction and magnetic induction speed of the capsule medical device 2 inside the three-dimensional space S, a direction and magnitude of magnetism acted to the capsule medical device 2 upon magnetic induction, an input amount of operation information of the magnetic induction, and the like.

The storage unit 6e is achieved using various memory media, such as a semiconductor memory, hard disk, or the like. The storage unit 6e stores a variety of information instructed to be stored by the magnetic induction controlling unit 6f, and sends out to the magnetic induction controlling unit 6f information instructed to be read by the magnetic induction controlling unit 6f among the stored variety of information. The variety of information stored by the storage unit 6e include, for example, the magnetic induction direction and magnetic induction speed of the capsule medical device 2 inside the three-dimensional space S, the position/direction information of the capsule medical device 2 detected (calculated) by the aforementioned position detecting device 3, and the like.

The magnetic induction controlling unit 6f controls an operation of each component unit (specifically, the magnetic field generator 6a, the power supply unit 6b for coil, the operating unit 6c, the display unit 6d, and the storage unit 6e) of the magnetic induction unit 6, and controls input and output of signals between respective component units. Specifically, the magnetic induction controlling unit 6f controls a magnetic field direction and a magnetic field strength of the three-dimensional magnetic field of the magnetic field generator 6a based on the operation information inputted by the operating unit 6c, and controls the magnetic induction of the capsule medical device 2. In this case, the magnetic induction controlling unit 6f acquires the position/direction information of the capsule medical device 2 from the aforementioned control unit 19 of the position detecting device 3, and refers to thus acquired position/direction information to control the magnetic induction of the capsule medical device 2. The magnetic induction controlling unit 6f controls an amount of current flow of the power supply unit 6b for coil to the magnetic field generator 6a, and controls the magnetic field direction and magnetic field strength of the three-dimensional magnetic field of the magnetic field generator 6a through control of this amount of current flow. In addition, the magnetic induction controlling unit 6f causes the display unit 6d to display information useful for the magnetic induction of the capsule medical device 2 according to a situation of the magnetic induction of the capsule medical device 2 inside the three-dimensional space S.

As described above, in the modified embodiment of the first embodiment of the present invention, a magnet for magnetic induction is further incorporated in a capsule medical device which is the detecting body, a magnetic induction unit for magnetically inducing the capsule medical device that incorporates the magnet in the three-dimensional space is further provided, and other configurations are similar to those of the first embodiment. As a result, operation effects similar to a case of the aforementioned first embodiment can be obtained, and position/direction information on the capsule medical device magnetically induced in a desired position and direction inside the three-dimensional space (specifically, inside the subject) can be detected, so that the position detecting system which can make use of the position/direction information for the magnetic induction of the capsule medical device can be achieved.

Next, a second embodiment of the present invention will be described. Although whenever the capsule medical device 2 captures the image in the body, the resonant state of the capsule medical device 2 is periodically released in the aforementioned first embodiment, the release of the resonant state of the capsule medical device is requested from the position detecting device side, and the capsule medical device releases the resonant state according to the request in the second embodiment.

Figure 10:
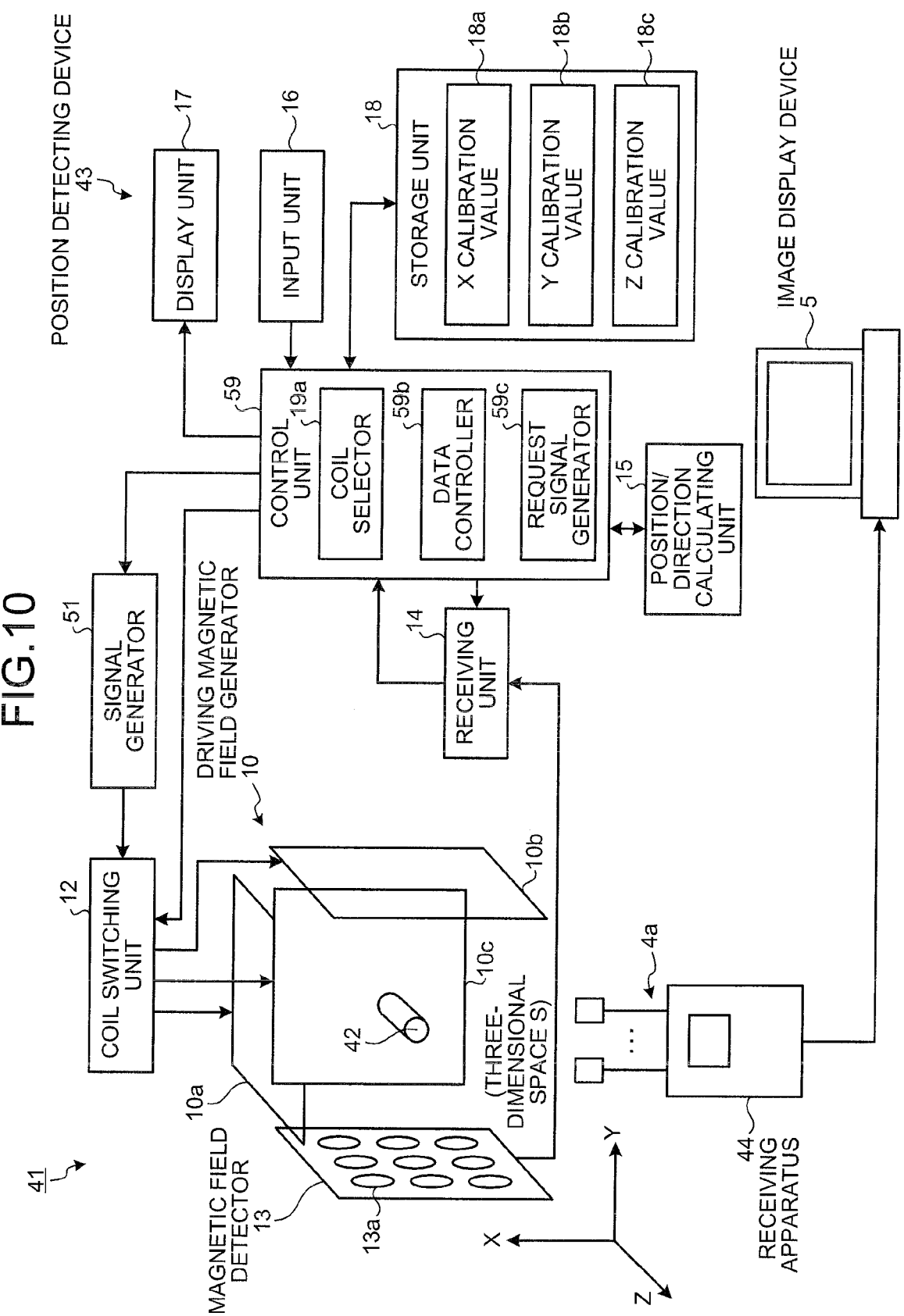
FIG. 10 is a block diagram schematically showing one configuration example of a position detecting system in accordance with a second embodiment of the present invention.

FIG. 10 is a block diagram schematically showing one configuration example of a position detecting system in accordance with the second embodiment of the present invention. As shown in FIG. 10, a position detecting system 41 in accordance with the second embodiment is provided with a capsule medical device 42 in place of the capsule medical device 2 of the position detecting system 1 in accordance with the aforementioned first embodiment, is provided with a position detecting device 43 in place of the position detecting device 3, and is provided with a receiving apparatus 44 in place of the receiving apparatus 4. The position detecting device 43 is provided with a signal generator 51 in place of the signal generator 11 of the position detecting device 3 in accordance with the aforementioned first embodiment, and is provided with a control unit 59 in place of the control unit 19. Additionally, in the position detecting system 41, the drive coils 10a to 10c of the driving magnetic field generator 10 combine the aforementioned driving magnetic field generation function, and a transmission antenna function for wirelessly transmitting the request signal of resonant state release to the capsule medical device 42. Other configurations are the same as those of the first embodiment, and the same reference numeral is given to the same configuration.

The capsule medical device 42 receives the request signal from the position detecting device 43 side via the drive coils 10a to 10c of the driving magnetic field generator 10 for every imaging operation of the image in the body of the subject, in place of periodically releasing the resonant state, and releases the resonant state based on thus received request signal. It is to be noted that other functions that the capsule medical device 42 has are similar to those of the capsule medical device 2 of the position detecting system 1 in accordance with the aforementioned first embodiment.

The receiving apparatus 44 has neither the aforementioned function for generating timing signal nor function for transmitting the timing signal to the position detecting device side, but has similar functions to those of the receiving apparatus 4 of the position detecting system 1 in accordance with the aforementioned first embodiment other than above functions.

The signal generator 51 combines an alternating current signal generating function similar to that of the signal generator 11 of the position detecting device 3 in accordance with the aforementioned first embodiment, and a modulation signal generator function for generating a modulation signal of the request signal for requesting the release of the resonant state of the capsule medical device 42. The signal generator 51 generates a modulation signal of the request signal instructed to be transmitted by the control unit 59, and transmits thus generated modulation signal to the coil switching unit 12. The modulation signal generated by the signal generator 51 is received by the capsule medical device 42 via any one of the drive coils 10a to 10c of the driving magnetic field generator 10, namely, the drive coil in the driving state selected by the coil selector 19a.

The control unit 59 has a coil selector 19a of the position detecting device 3 in accordance with the aforementioned first embodiment, has a data controller 59b in place of the data controller 19b, and further has a request signal generator 59c. The data controller 59b sequentially acquires the magnetic field detection data of the magnetic field detector 13 via the receiving unit 14 while monitoring an output of the request signal of the resonant state release. The data controller 59b sequentially determines whether to employ or to discard the magnetic field detection data based on an output timing of the request signal. The request signal generator 59c to which a predetermined time is set previously periodically generates the request signal of the resonant state release, whenever this set time elapses. The set time of the request signal generator 59c can be set as a desired time based on input information of the input unit 16. The control unit 59 transmits the request signal generated by the request signal generator 59c to the signal generator 51, and controls the signal generator 51 to output the modulation signal of the transmitted request signal. It is to be noted that other functions that the control unit 59 has are similar to those of control unit 19 of the position detecting device 3 in accordance with the aforementioned first embodiment.

Figure 11:
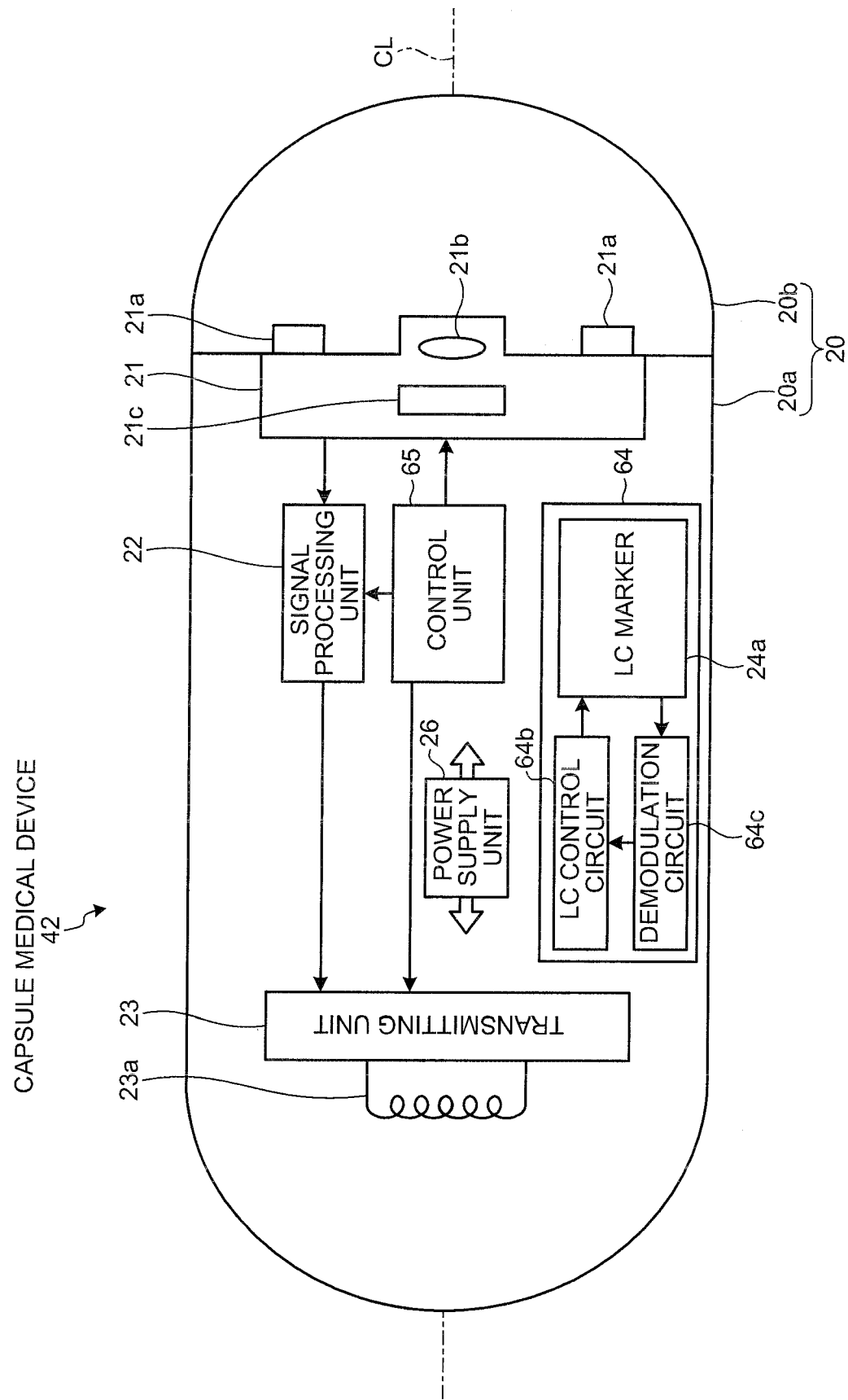
FIG. 11 is a schematic view showing one configuration example of a capsule medical device of the position detecting system in accordance with the second embodiment of the present invention.

Next, a configuration of the capsule medical device 42 of the position detecting system 41 in accordance with the second embodiment of the present invention will be described in detail. FIG. 11 is a schematic view showing one configuration example of a capsule medical device of the position detecting system in accordance with the second embodiment of the present invention. As shown in FIG. 11, the capsule medical device 42 in accordance with the second embodiment is provided with a resonance magnetic field generator 64 in place of the resonance magnetic field generator 24 of the capsule medical device 2 in accordance with the aforementioned first embodiment, and is provided with a control unit 65 in place of the control unit 25. Other configurations are the same as those of the first embodiment, and the same reference numeral is given to the same configuration.

The resonance magnetic field generator 64 is provided with the LC marker 24a of the capsule medical device 2 in accordance with the aforementioned first embodiment, is provided with an LC control circuit 64b in place of the LC control circuit 24b, and is further provided a demodulation circuit 64c for demodulating the aforementioned modulation signal of the request signal. It is to be noted that in the resonance magnetic field generator 64, the LC marker 24a combines the aforementioned generating function of the resonance magnetic field, and a function as a receiving antenna for receiving the modulation signal of the request signal generated by the signal generator 51. The demodulation circuit 64c demodulates the modulation signal from the position detecting device 43 received by the LC marker 24a into the request signal of the resonant state release, and transmits the request signal thus obtained to the LC control circuit 64b. The LC control circuit 64b controls switching between the resonant state and the non-resonant state of the LC marker 24a. The LC control circuit 64b releases the resonant state of the LC marker 24a to switch it to the non-resonant state based on the request signal of the resonant state release acquired from the demodulation circuit 64c, and maintains this non-resonant state of the LC marker 24a during a predetermined period. Subsequently, the LC control circuit 64b switches the non-resonant state of the LC marker 24a to the resonant state thereof.

The control unit 65 does not have a function to instruct the release of the resonant state for every imaging timing of the image in the body, but has functions similar to those of the control unit 25 of the capsule medical device 2 in accordance with the aforementioned first embodiment, other than this function. Namely, the control function of the control unit 65 does not contribute to the release of the resonant state function of the LC marker 24a.

Figure 12:
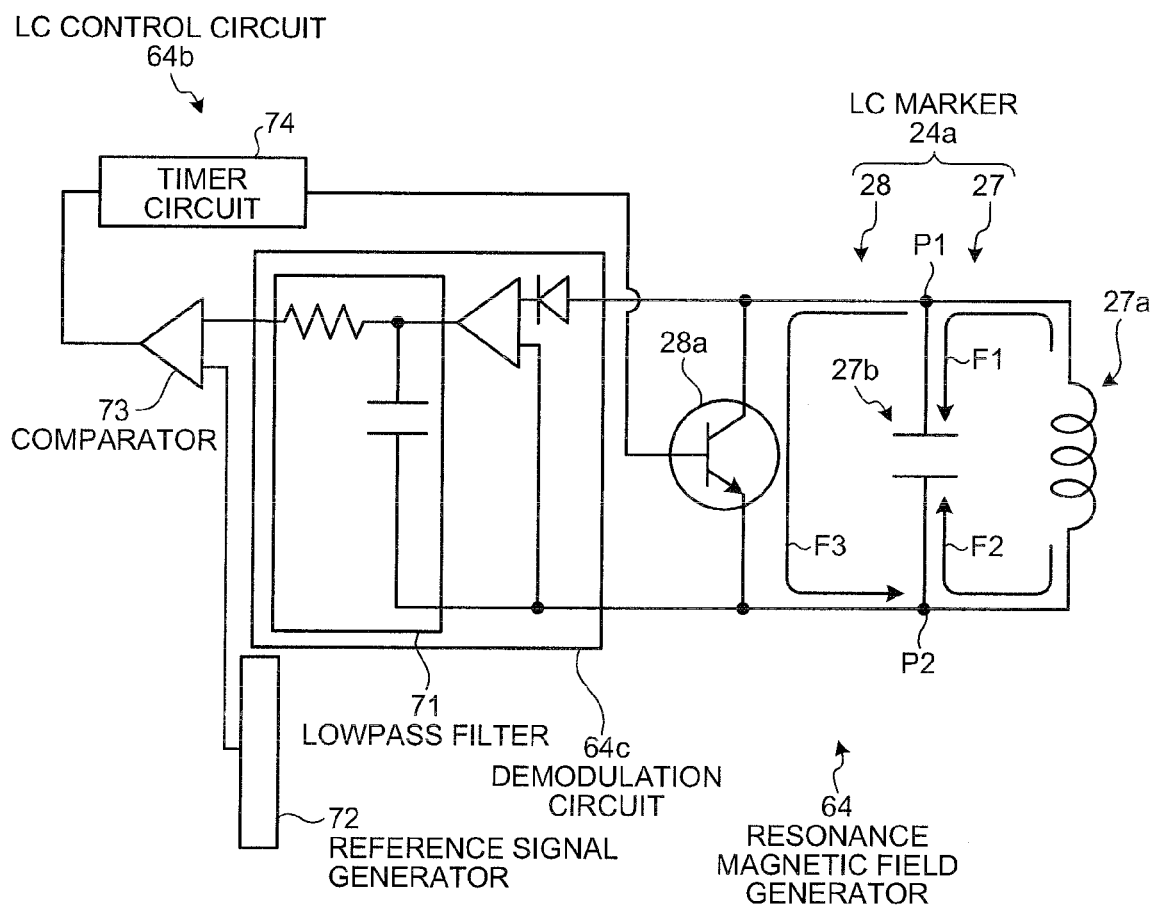
FIG. 12 is a schematic view showing one circuit configuration example of a resonance magnetic field generator of the capsule medical device in accordance with the second embodiment of the present invention.

Next, the resonance magnetic field generator 64 of the capsule medical device 42 will be described in detail. FIG. 12 is a schematic view showing one circuit configuration example of a resonance magnetic field generator of the capsule medical device in accordance with the second embodiment of the present invention. The resonance magnetic field generator 64 is provided with the LC marker 24a, the LC control circuit 64b, and the demodulation circuit 64c as described above.

Specifically, as shown in FIG. 12, the LC control circuit 64b is achieved using a reference signal generator 72 for generating a predetermined reference signal, a comparator 73 for comparing the reference signal with a signal from the demodulation circuit 64c, and a timer circuit 74 for releasing the resonant state of the LC marker 24a during a predetermined period based on an output signal from the comparator 73. The demodulation circuit 64c is achieved by a circuit configuration using a lowpass filter 71 or the like. It is to be noted that the LC marker 24a has a circuit configuration based on the parallel connection of the LC resonance circuit 27 and the current bypass circuit 28, which is substantially similar to the case of the aforementioned first embodiment.

In the resonance magnetic field generator 64, the LC resonance circuit 27 receives by the coil 27a the modulation signal from the position detecting device 43 transmitted by the magnetic field of the aforementioned drive coils 10a to 10c, and transmits the modulation signal thus received to the demodulation circuit 64c via the current bypass circuit 28. It is to be noted that the modulation signal from the position detecting device 43 is a signal into which the request signal of the resonant state release of the LC marker 24a (specifically, LC resonance circuit 27) is modulated. The demodulation circuit 64c demodulates the modulation signal from the position detecting device 43 received from the LC marker 24a into the request signal of the resonant state release, and transmits the request signal thus obtained to the comparator 73 of the LC control circuit 64b.

In the LC control circuit 64b, the comparator 73 compares the signal from the demodulation circuit 64c with the reference signal from the reference signal generator 72, and transmits a control signal at high level or low level to the timer circuit 74 depending on the comparison result. Specifically, if the comparator 73 acquires from the demodulation circuit 64c a signal higher than the reference signal from the reference signal generator 72, it outputs a low level control signal to the timer circuit 74. Meanwhile, if the comparator 73 acquires from the demodulation circuit 64c a signal (namely, request signal of the resonant state release demodulated by the demodulation circuit 64c) lower than the reference signal from the reference signal generator 72, it outputs a high level control signal to the timer circuit 74.

The timer circuit 74 to which a predetermined time is previously set puts the LC resonance circuit 27 into the resonant state or the non-resonant state based on the control signal from the comparator 73. Specifically, if the timer circuit 74 acquires the low level control signal from the comparator 73, it does not apply a base current to the switching element 28a of the current bypass circuit 28 to thereby maintain the LC resonance circuit 27 in the resonant state. Meanwhile, if the timer circuit 74 acquires the high level control signal from the comparator 73, it applies the base current to the switching element 28a of the current bypass circuit 28 and maintains a state of applying the base current until the set time elapses. Thereby, the timer circuit 74 releases the resonant state of the LC resonance circuit 27 to switch it to the non-resonant state, and maintains this non-resonant state during a predetermined period. Subsequently, the timer circuit 74 stops applying the base current to the switching element 28a, and thereby switches the LC resonance circuit 27 into the resonant state.

Figure 13:
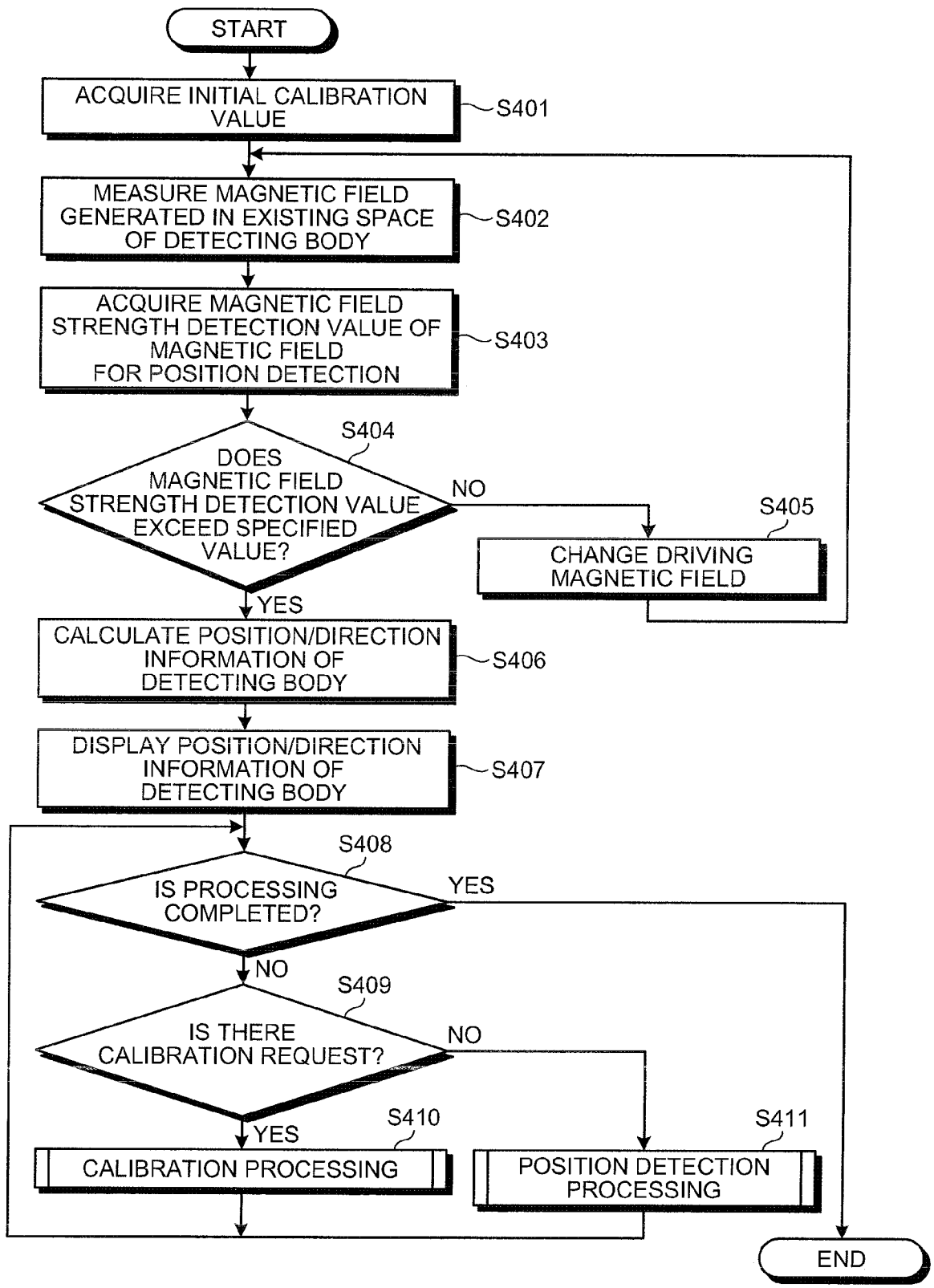
FIG. 13 is a flow chart illustrating a procedure of a position detecting device upon detecting a position and a direction of the capsule medical device which is a detecting body inside three-dimensional space.

Next, an operation of the position detecting system 41 in accordance with the second embodiment of the present invention will be described. FIG. 13 is a flow chart illustrating a procedure of the position detecting device upon detecting the position and direction of the capsule medical device 42 which is the detecting body inside the three-dimensional space S.

As shown in FIG. 13, the control unit 59 of the position detecting device 43 first acquires an initial calibration value of each of the drive coils 10a to 10c of the driving magnetic field generator 10 in a manner similar to that at aforementioned Steps S101 through S103 shown in FIG. 5 (Step S401), measures a magnetic field generated in the three-dimensional space S which is an existing space of the capsule medical device 42 after the capsule medical device 42 is introduced into the inside of the three-dimensional space S (specifically, inside of the subject) (Step S402), and subsequently acquires a magnetic field strength detection value of the magnetic field for position detection of the capsule medical device 42 inside the three-dimensional space S (Step S403).

Next, the control unit 59 determines whether or not the magnetic field strength detection value of the resonance magnetic field acquired (calculated) at Step S403 exceeds a predetermined specified value in a manner similar to aforementioned Step S104 (Step S404), and if the magnetic field strength detection value of the resonance magnetic field is the specified value or less (Step S404, No), it changes the driving magnetic field actually generated in the three-dimensional space S in a manner similar to aforementioned Step S105 (Step S405). Subsequently, the control unit 59 returns to aforementioned Step S402, and repeats the procedure after Step S402.

Meanwhile, if the magnetic field strength detection value of the resonance magnetic field exceeds the specified value at Step S404 (Step S404, Yes), the control unit 59 determines that this magnetic field strength detection value of the resonance magnetic field is a sufficient value as the magnetic field for position detection, calculates position/direction information of the detecting body based on the magnetic field strength detection value of the resonance magnetic field in a manner similar to aforementioned Steps S106 and S107 (Step S406), and displays the position/direction information of the detecting body thus calculated on the display unit 17 (Step S407).

Subsequently, the control unit 59 determines whether or not the processing is completed in a manner similar to that at aforementioned Step S108 (Step S408), and if the processing is completed (Step S408, Yes), it completes the present processing. Meanwhile, if the processing is not completed at Step S408 (Step S408, No), the control unit 59 determines whether or not there is a calibration request for requesting acquisition and update of the calibration value which is the reference value of the position/direction calculating processing (Step S409).

At Step S409, if a predetermined time has elapsed after acquiring and updating the calibration value last time, the control unit 59 determines that there is the calibration request, whereas if the predetermined time has not yet elapsed, it determines that there is no calibration request. If there is the calibration request (Step S409, Yes), the control unit 59 requests the resonant state release of the capsule medical device 42 to execute the calibration processing for acquiring and updating the calibration value of the position/direction calculating processing (Step S410), and subsequently, returns to aforementioned Step S408 to repeat the procedure after Step S408. Meanwhile, if there is no calibration request (Step S409, No), the control unit 59 uses the existing calibration value to execute the position detection processing for calculating the position/direction information on the capsule medical device 42 (Step S411), and subsequently, returns to aforementioned Step S408 to repeat the procedure after Step S408.

It is to be noted that the control unit 59 may add determination processing for determining whether or not the driving magnetic field change is required in a manner similar to aforementioned Step S109 in the procedure at aforementioned Steps S408 through S411, and may execute the drive coil switching processing in a manner similar to aforementioned Step S111, if it determines that the driving magnetic field change is required based on this determination processing.

Figure 14:
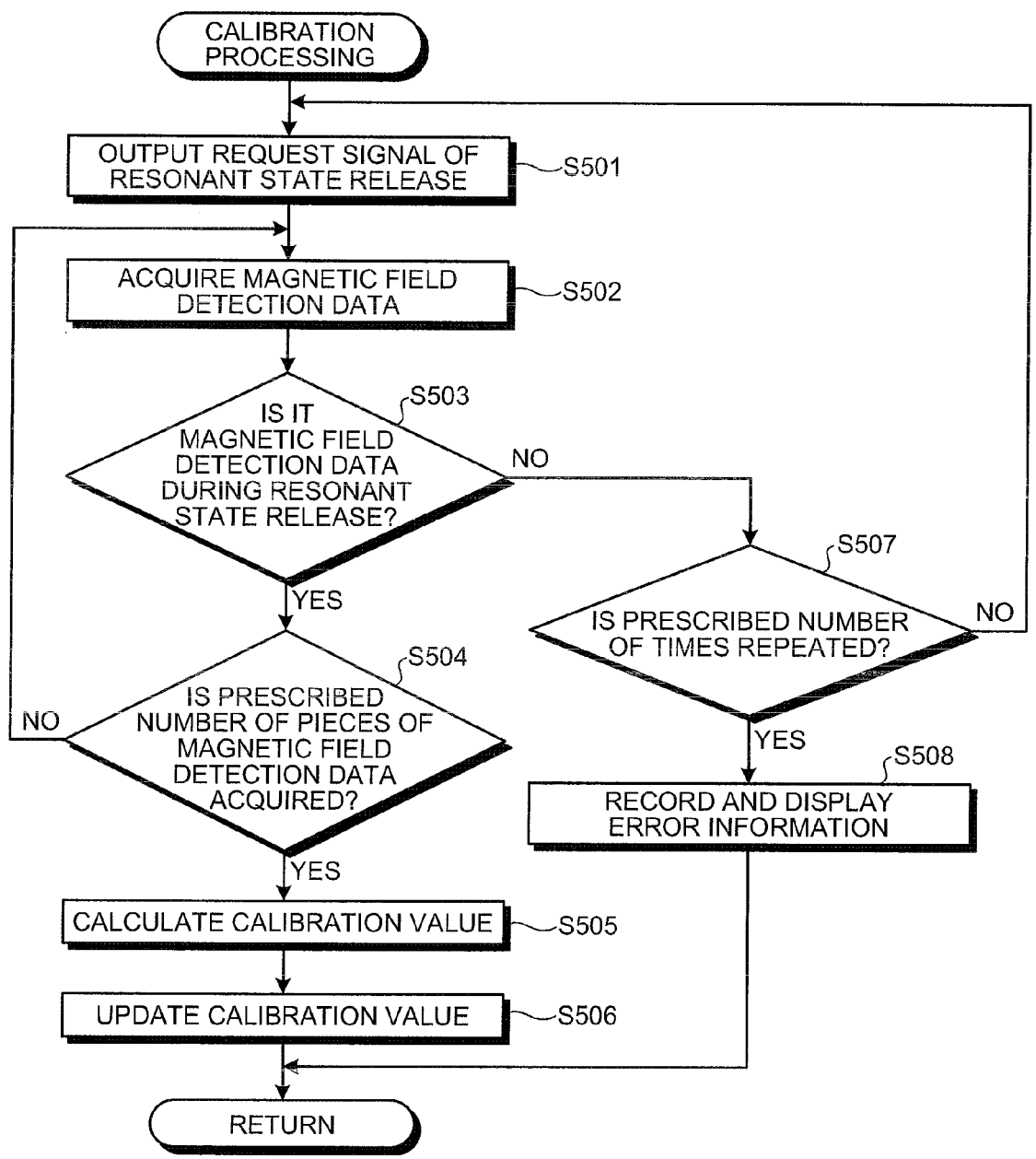
FIG. 14 is a flow chart illustrating a procedure of calibration processing of the position detecting system in accordance with the second embodiment of the present invention.

Next, the calibration processing at aforementioned Step S410 will be described in detail. FIG. 14 is a flow chart illustrating a procedure of calibration processing of the position detecting system in accordance with the second embodiment of the present invention.

In the calibration processing at aforementioned Step S410, the control unit 59 of the position detecting device 43 first outputs the request signal of the resonant state release to the capsule medical device 42 inside the three-dimensional space S as shown in FIG. 14 (Step S501). At Step S501, the request signal generator 59c generates the request signal of the resonant state release at a time interval previously set. It is to be noted that the request signal generated by the request signal generator 59c is a signal for requesting the release of the resonant state to the capsule medical device 42 inside the three-dimensional space S. The control unit 59 controls the signal generator 51 to generate and output the modulation signal of the request signal of the resonant state release. The modulation signal of the request signal is transmitted to the capsule medical device 42 inside the three-dimensional space S via the drive coil in the driving state (any one of the drive coils 10a to 10c) as described above.

Next, the control unit 59 acquires the magnetic field detection data of the magnetic field detector 13 via the receiving unit 14 (Step S502), and determines whether or not the magnetic field detection data thus acquired is the magnetic field detection data during the resonant state release (Step S503). At Steps S502 and S503, the data controller 59b acquires the magnetic field detection data inside the three-dimensional space S detected by the magnetic field detector 13, and compares the magnetic field detection data thus acquired with the magnetic field detection data during the position detection.

Here, the magnetic field detection data during the position detection is the magnetic field detection data used for the position/direction calculating processing of the capsule medical device 42, and is the magnetic field detection data of the spatial magnetic field inside the three-dimensional space S, including the resonance magnetic field from the capsule medical device 42 and the environmental magnetic field. The magnetic field detection data acquired at Step S502 differs from the magnetic field detection data during the position detection, if it is the magnetic field detection data during the resonant state release of the capsule medical device 42. If the magnetic field detection data thus acquired differs from the magnetic field detection data during the position detection, the data controller 59b determines that it is the magnetic field detection data during the resonant state release of the capsule medical device 42 based on this, whereas if the magnetic field detection data thus acquired is substantially the same as the magnetic field detection data during the position detection, it determines that it is the magnetic field detection data during the resonant state of the capsule medical device 42 (namely, magnetic field detection data of the spatial magnetic field inside the three-dimensional space S, including the resonance magnetic field from the capsule medical device 42 and the environmental magnetic field).

If the magnetic field detection data acquired at Step S502 is the magnetic field detection data during the resonant state release (Step S503, Yes), the control unit 59 determines whether or not the magnetic field detection data during the resonant state release is acquired by a prescribed number previously set (Step S504). If the magnetic field detection data during the resonant state release is not acquired by the predetermined prescribed number (Step S504, No), the control unit 59 returns to aforementioned Step S502, and repeats the procedure after Step S502.

Meanwhile, if the magnetic field detection data during the resonant state release is acquired by the predetermined prescribed number (Step S504, Yes), the control unit 59 calculates the calibration value of the position/direction calculating processing based on the prescribed number of pieces of magnetic field detection data during the resonant state release thus acquired (Step S505). At Step S505, the control unit 59 performs equalizing processing on the prescribed number of pieces of magnetic field detection data during the resonant state release, and acquires a mean value of the magnetic field detection data during the resonant state release thus obtained as the calibration value corresponding to the drive coil actually in the driving state.

Subsequently, the control unit 59 performs the update processing of the calibration value calculated at Step S505 (Step S506) to then return to aforementioned Step S410. At Step S506, the control unit 59 overwrites the calibration value on the storage unit 18 at Step S505 as up-to-date information on the calibration value corresponding to the drive coil in the driving state selected by the coil selector 19a. Thereby, the calibration value (detailedly, any one of the X calibration value 18*a*, the Y calibration value 18*b*, and the Z calibration value 18*c*) in the storage unit 18 is updated to the up-to-date information.

Meanwhile, if the magnetic field detection data acquired at Step S502 is not the magnetic field detection data during the resonant state release (Step S503, No), the control unit 59 determines whether or not the procedure at aforementioned Steps S501 through S503 is repeated by the predetermined prescribed number of times (Step S507). If the procedure at Steps S501 through S503 is not yet repeated by the prescribed number of times (Step S507, No), the control unit 59 returns to aforementioned Step S501, and repeats the procedure after Step S501. Meanwhile, if the procedure at Steps S501 through S503 is repeated by the prescribed number of times (for example, 3 times) (Step S507, Yes), the control unit 59 displays on the display unit 17 error information for indicating that the resonant state of the capsule medical device 42 is not released, and also records this error information on the storage unit 18 (Step S508). Subsequently, the control unit 59 returns to aforementioned Step S410.

Figure 15:
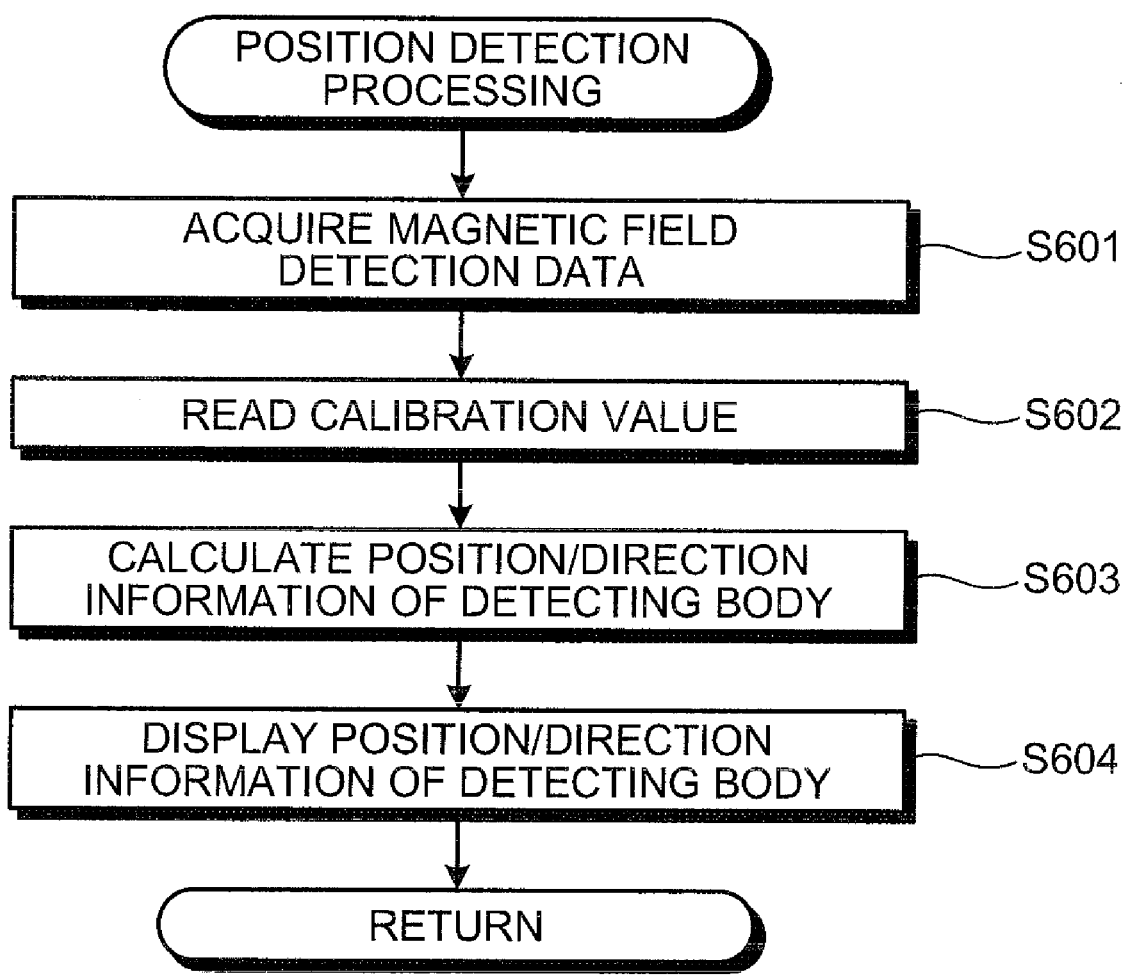
FIG. 15 is a flow chart illustrating a procedure of position detection processing of the position detecting system in accordance with the second embodiment of the present invention.

Next, the position detection processing at aforementioned Step S411 will be described in detail. FIG. 15 is a flow chart illustrating a procedure of position detection processing of the position detecting system in accordance with the second embodiment of the present invention. In the position detection processing at aforementioned Step S411, the control unit 59 of the position detecting device 43 first acquires the magnetic field detection data of the magnetic field detector 13 via the receiving unit 14 as shown in FIG. 15 (Step S601).

Here, the magnetic field detection data acquired at Step S601 is data detected by the magnetic field detector 13 if the capsule medical device 42 inside the three-dimensional space S is in the resonant state, and is the magnetic field detection data of the spatial magnetic field inside the three-dimensional space S, including the resonance magnetic field from the capsule medical device 42 and the environmental magnetic field. The data controller 59*b* employs the magnetic field detection data acquired at Step S601 as operation data of the position/direction calculating processing of the position/direction calculating unit 15.

Next, the control unit 59 reads the calibration value used for the position/direction calculating processing of the position/direction calculating unit 15 from the storage unit 18 (Step S602). At Step S602, the control unit 59 reads the calibration value corresponding to the drive coil actually in the driving state selected by the coil selector 19*a* among the X calibration value 18*a*, the Y calibration value 18*b*, and the Z calibration value 18*c* in the storage unit 18. Specifically, the control unit 59 reads the X calibration value 18*a* from the storage unit 18, if the drive coil 10*a* is the drive coil in the driving state; reads the Y calibration value 18*b* from the storage unit 18, if the drive coil 10*b* is the drive coil in the driving state; and reads the Z calibration value 18*c* from the storage unit 18, if the drive coil 10*c* is the drive coil in the driving state.

Subsequently, the control unit 59 calculates the position/direction information of the detecting body, namely, the position/direction information on the capsule medical device 42 inside the three-dimensional space S (Step S603). At Step S603, the control unit 59 transmits to the position/direction calculating unit 15 the magnetic field detection data (specifically, magnetic field strength detection value of the spatial magnetic field inside the three-dimensional space S) at Step S601 and the calibration value at Step S602, and controls the position/direction calculating unit 15 to execute the position/direction calculating processing of the capsule medical device 42 using the transmitted magnetic field detection data and calibration value. The control unit 59 acquires the calculation result (namely, position/direction information on the capsule medical device 42 inside the three-dimensional space S) of the position/direction calculating unit 15.

Next, the control unit 59 displays on the display unit 17 the position/direction information of the detecting body calculated at Step S603, namely, the position/direction information of the capsule medical device 42 inside the three-dimensional space S (Step S604), and subsequently returns to aforementioned Step S411. At Step S604, the control unit 59 displays on the display unit 17 the current position/direction information of the capsule medical device 42 which is the detecting body inside the three-dimensional space S to thereby update the display information on this display unit 17 (position/direction information of the capsule medical device 42, track information of the capsule medical device 42, and the like) to the up-to-date information.

Figure 16:
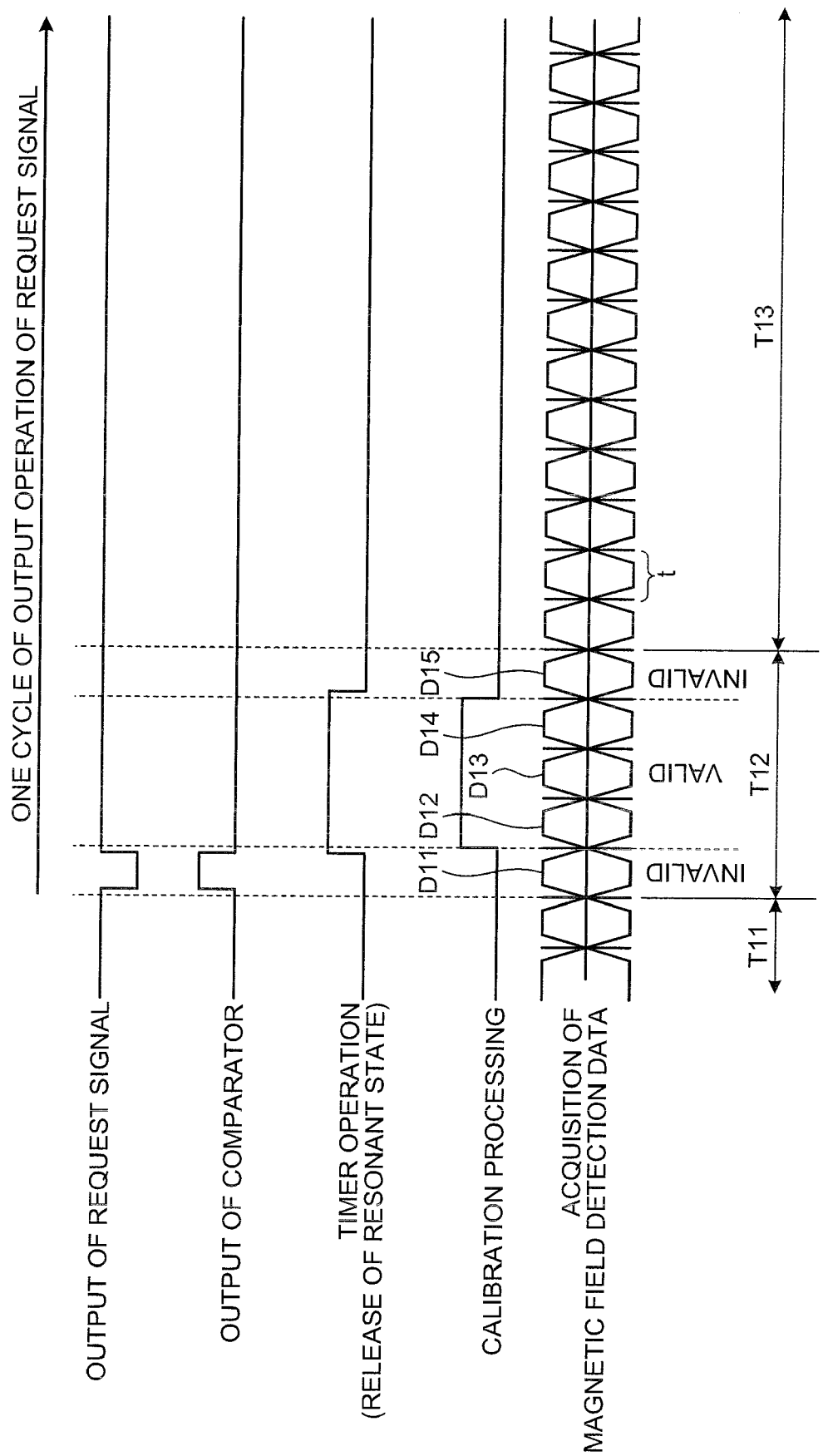
FIG. 16 is a timing chart for specifically explaining an operation of the position detecting system in accordance with the second embodiment of the present invention.

Next, while illustrating one cycle of an output operation of the request signal for requesting the resonant state release of the capsule medical device 42 inside the three-dimensional space S (specifically, inside the subject), the operation of the position detecting system 41 in accordance with the second embodiment of the present invention will be described concretely. FIG. 16 is a timing chart for specifically explaining an operation of the position detecting system in accordance with the second embodiment of the present invention. It is to be noted that in FIG. 16, each timing chart of "output of request signal", "calibration processing", and "acquisition of magnetic field detection data" indicates an operation timing of the control unit 59 of the position detecting device 43 in the position detecting system 41, and each timing chart of "output of comparator" and "timer operation" indicates an operation timing of the capsule medical device 42 in the position detecting system 41.

The position detecting device 43 successively detects the magnetic field in the three-dimensional space S by the magnetic field detector 13, while suitably switching the drive coil in the driving state among the drive coils 10*a* to 10*c* of the driving magnetic field generator 10. In the position detecting device 43, the control unit 59 sequentially acquires the magnetic field detection data of the magnetic field detector 13 for every unit time t as shown in FIG. 16.

In addition, the position detecting device 43 outputs the request signal for requesting the release of the resonant state of the capsule medical device 42 at predetermined timing. In the position detecting device 43, the request signal generator 59*c* periodically generates the request signal of the resonant state release at a predetermined time interval, and the control unit 59 controls the signal generator 51 to output the request signal of the resonant state release. The signal generator 51 outputs the modulation signal, into which the request signal of the resonant state release is modulated, to the driving magnetic field generator 10 via the coil switching unit 12. The modulation signal is transmitted to the capsule medical device 42 inside the three-dimensional space S by changing the driving magnetic field of the drive coil actually in the driving state (any one of the drive coils 10*a* to 10*c*) for a short time (for example, put it into a zero magnetic field for a short time).

The capsule medical device 42 inside the three-dimensional space S receives from the position detecting device 43 the modulation signal transmitted by changing the driving magnetic field for a short time. In the capsule medical device 42, the LC marker 24*a* receives the modulation signal from the position detecting device 43, and the demodulation circuit 64*c* demodulates the modulation signal received by this LC marker 24*a* into the request signal of the resonant state release. The comparator 73 of the LC control circuit 64b transmits a high level control signal to the timer circuit 74 in response to the request signal of the resonant state release.

The timer circuit 74 releases the resonant state of the LC marker 24a based on the high level control signal received from the comparator 73 to switch it to the non-resonant state, and maintains the non-resonant state for a predetermined period. In this case, the timer circuit 74 continues applying the base current to the switching element 28a of the LC marker 24a to maintain it in a state where a current can be made to flow through the current bypass circuit 28 during a period after receiving the high level control signal until a predetermined time elapses to thereby continue releasing the resonant state of the LC resonance circuit 27 (refer to FIG. 12).

It is to be noted that the timer circuit 74 maintains the non-resonant state of the LC marker 24a during a period more than twice the acquisition period (unit time t) of the magnetic field detection data by the control unit 59, desirably during a period three times longer than that. As a result, the control unit 59 of the position detecting device 43 will be able to reliably acquire one or a plurality of pieces of magnetic field detection data of the environmental magnetic field inside the three-dimensional space S within a period when the LC marker 24a is in the non-resonant state.

Meanwhile, the position detecting device 43 sequentially acquires a plurality of pieces of magnetic field detection data D11 to D15 during a period T12 after outputting the request signal of the resonant state release to the capsule medical device 42 until a predetermined time elapses. In the position detecting device 43, the data controller 59b discards the magnetic field detection data D11 acquired at the first period T12 and the magnetic field detection data D15 acquired at last period among a plurality of pieces of magnetic field detection data D11 to D15 in consideration of operational variation of the aforementioned timer circuit 74 to thereby make them as invalid data. Meanwhile, the data controller 59b employs the magnetic field detection data D12, D13, and D14 as valid data acquired from the timing after the unit time t elapses since the start of the period T12 until a timing back to from completion of the period T12 by the unit time t.

It is to be noted that the period from the timing after the unit time t elapses from the start of the period T12 until the timing back to from the completion of the period T12 by the unit timing t is substantially the same as a period when a state of releasing the resonant state of the LC resonance circuit 27 of the capsule medical device 42 (namely, non-resonant state) is maintained.

The control unit 59 acquires the valid magnetic field detection data D12, D13, and D14 (namely, magnetic field strength detection value of the environmental magnetic field which is the magnetic field inside the three-dimensional space S excluding the resonance magnetic field from the capsule medical device 42) during the period T12, and performs the equalizing processing on the magnetic field detection data D12, D13, and D14 thus acquired. The control unit 59 overwrites a mean value of the magnetic field detection data D12, D13, and D14 on the storage unit 18 as the calibration value corresponding to the drive coil actually in the driving state. Specifically, the control unit 59 overwrites the mean value of the magnetic field detection data D12, D13, and D14 on the storage unit 18 as the X calibration value 18a corresponding to the drive coil 10a, if the drive coil 10a is in the driving state; overwrites the mean value of the magnetic field detection data D12, D13, and D14 on the storage unit 18 as the Y calibration value 18b corresponding to the drive coil 10b, if the drive coil 10b is in the driving state; and overwrites the mean value of the magnetic field detection data D12, D13, and D14 on the storage unit 18 as the Z calibration value 18c corresponding to the drive coil 10c, if the drive coil 10c is in the driving state. Thus, the control unit 59 achieves the update processing (calibration processing) of the calibration value corresponding to the drive coil in the driving state. It is to be noted that the control unit 59 forbids the position/direction calculating processing of the position/direction calculating unit 15 during the period T12 for executing the calibration processing.

Meanwhile, the control unit 59 sequentially acquires the magnetic field detection data of the magnetic field detector 13 for every unit time t during the periods T11 and T13 when the LC marker 24a of the capsule medical device 42 is in the resonant state. Here, the magnetic field detection data of the magnetic field detector 13 during the periods T11 and T13 is the detection data of the spatial magnetic field inside the three-dimensional space S (specifically, magnetic field strength detection value), including the resonance magnetic field from the capsule medical device 42 and the environmental magnetic field. The data controller 59b employs the magnetic field detection data during the periods T11 and T13 as the valid data for the position/direction calculating processing of the position/direction calculating unit 15. The control unit 59 transmits to the position/direction calculating unit 15 the magnetic field strength detection value of the spatial magnetic field which is the magnetic field detection data during the periods T11 and T13, and the calibration value corresponding to the drive coil actually in the driving state. The control unit 59 causes the position/direction calculating unit 15 to execute the position/direction calculating processing using the transmitted magnetic field strength detection value and calibration value in a manner similar to the aforementioned first embodiment.

The above position detecting system 41 operates in a manner similar to that of the cases of the periods T12 and T13 also during periods after the aforementioned period T13. Namely, the position detecting system 41 sequentially detects (calculates) the position/direction information of the capsule medical device 42 inside the three-dimensional space S during a period when the capsule medical device 42 is in the resonant state. In addition, the position detecting system 41 sequentially transmits the request signal of the resonant state release to the capsule medical device 42 at a predetermined time interval to periodically release the resonant state of the capsule medical device 42, and updates the calibration value of the position/direction calculating processing within the period when this resonant state is released.

As described above, in the second embodiment of the present invention, a position detecting device transmits to a capsule medical device a request signal for requesting release of a resonant state of the capsule medical device which is a detecting body at a predetermined time interval, the capsule medical device releases the resonant state during a predetermined period based on the request signal, and other configurations are substantially similar to those of the first embodiment. For this reason, operation effects similar to the case of the aforementioned first embodiment can be obtained, and calibration values of the position/direction calculating processing can also be acquired and updated periodically at a desired timing irrespective of a periodical operation, such as the imaging operation of the capsule medical device and the like, thus allowing the number of pieces of invalid magnetic field detection data to be reduced, and also position detection accuracy of the capsule medical device to be further improved by the calibration values acquired and updated at the required time.

In addition, since the LC resonance circuit incorporated in the capsule medical device is functioned as the receiving antenna for the request signal of the resonant state release, it is not necessary to add a receiving antenna for receiving the request signal of the resonant state release to the inside of the capsule medical device, thus allowing a circuit configuration inside the capsule medical device to be further simplified, and also reduction in size of the capsule medical device to be promoted.

Further, since the resonant state of the capsule medical device is released based on the request signal from the position detecting device irrespective of a periodical operation of the capsule medical devices, such as the imaging operation of the image in the body and the like, the operation of the capsule medical device can be simplified, thus allowing the internal configuration of the capsule medical device to be easily achieved.

In addition, since the drive coil for generating the driving magnetic field inside three-dimensional space is functioned as a transmission antenna for transmitting the request signal of the resonant state release, it is not necessary to add a transmission antenna for transmitting the request signal of the resonant state release to the capsule medical device inside three-dimensional space, thus allowing the position detecting system to be achieved by a simpler system configuration.

It is to be noted that a transistor is used as the switching element 28*a* of the current bypass circuit 28 for forming the alternative path of the current in the LC resonance circuit 27 in the first and second embodiments, and the modified embodiment of the present invention, but not limited to this, a field-effect transistor (FET) may be used as the switching element of the current bypass circuit 28, or a photo coupler may be used for it. In addition, the transistor for achieving the switching element 28*a* may be a PNP type transistor or an NPN type transistor. When the photo coupler is used as this switching element, it is possible to insulate the LC resonance circuit 27 from internal circuits (imaging unit 21 and the like) of the capsule medical device, thus allowing noise in the internal circuit of the capsule medical device to be further reduced.

Figure 17:
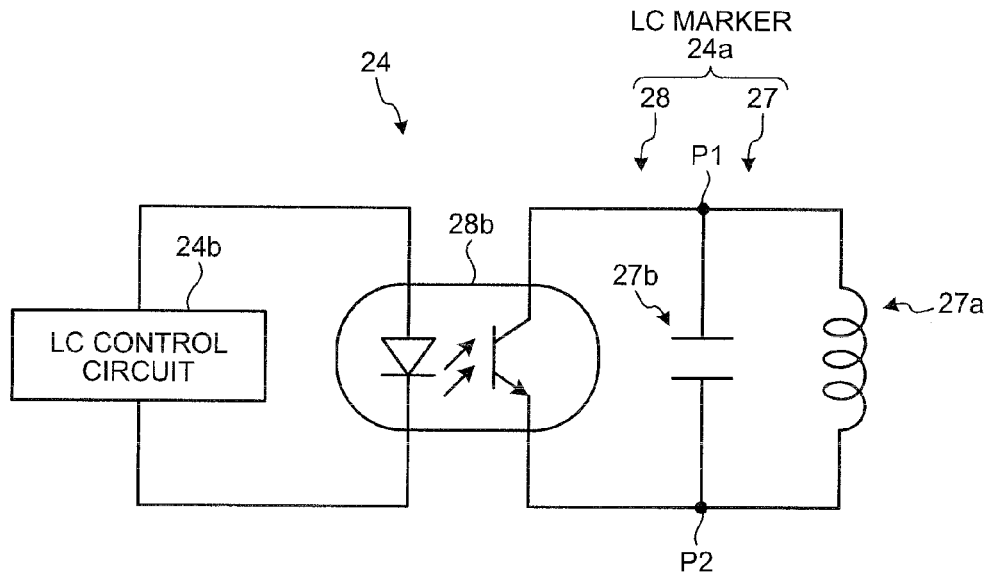
FIG. 17 is a schematic view showing a modified embodiment of the resonance magnetic field generator inside the capsule medical device.
Figure 18:
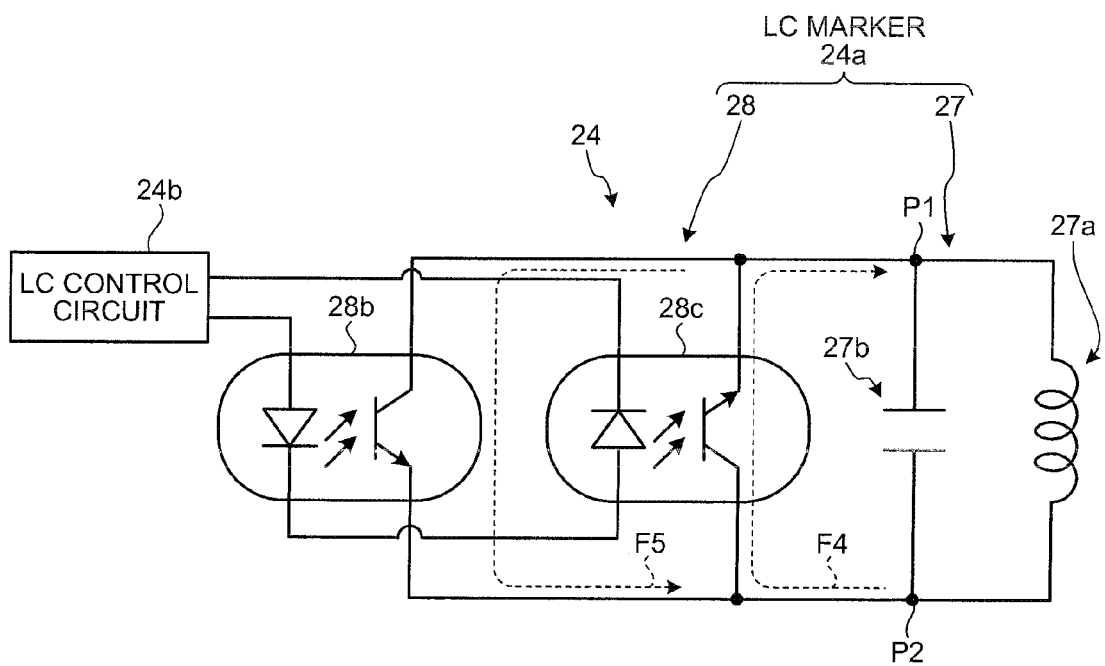
FIG. 18 is a schematic view showing another modified embodiment of the resonance magnetic field generator inside the capsule medical device.

Here, when a photo coupler is used as the switching element of the current bypass circuit 28, the circuit configuration of the resonance magnetic field generator 24 may be a circuit configuration using the photo coupler as a switching element 28*b* of the current bypass circuit 28 as shown in FIG. 17, for example, or may be a circuit configuration using two photo couplers as switching elements 28*b* and 28*c* of the current bypass circuit 28 as shown in FIG. 18, for example. When the resonance magnetic field generator 24 has the circuit configuration shown in FIG. 17, operation effects similar to the cases of the aforementioned first and second embodiments and modified embodiment are obtained. Meanwhile, when the resonance magnetic field generator 24 has the circuit configuration shown in FIG. 18, the alternating current generated by the coil 27*a* in response to the driving magnetic field can be made to flow through alternative paths F4 and F5 of the current bypass circuit 28 to thereby allow the current in the LC resonance circuit 27 to be diverted in the current bypass circuit 28 more reliably, so that the resonant state of the LC resonance circuit 27 can be released more reliably.

Moreover, the calibration value of the position/direction calculating processing is acquired and updated using one piece of magnetic field detection data detected during the period when the resonant state of the LC resonance circuit is released in the first embodiment and the modified embodiment of the present invention, but not limited to this, one or more pieces of magnetic field detection data (magnetic field detection data of the environmental magnetic field) may be sequentially acquired during the period of maintaining the non-resonant state of the LC resonance circuit, which is periodically repeated, the magnetic field detection data of prescribed number of times (for example, 10 times) previously set may be accumulated to perform moving average processing on the magnetic field detection data by the prescribed number of times, and the calculation result of this moving average processing may be acquired and updated as the calibration value of the position/direction calculating processing.

Further, the calibration value of the position/direction calculating processing is acquired and updated using one piece of valid magnetic field detection data (magnetic field detection data of the environmental magnetic field) detected during the period when the resonant state of the LC resonance circuit is released in the first embodiment and the modified embodiment of the present invention, but not limited to this, the resonant state release period may be adjusted (increased) so that a plurality of pieces of valid magnetic field detection data can be acquired during one resonant state release period (period of maintaining the non-resonant state) of the LC resonance circuit, and one calibration value may be acquired and updated using a plurality of pieces of valid magnetic field detection data.

Moreover, the resonant state of the LC resonance circuit inside the capsule medical device is released in synchronization with the imaging timing of the image in the body by the capsule medical device in the first embodiment and the modified embodiment of the present invention, but not limited to this, a timer unit for instructing the release of the resonant state timing to the LC control circuit at a time interval previously set may be incorporated in the capsule medical device, and the resonant state of the LC resonance circuit may be periodically released for every set time of this timer unit. In this case, the timer unit may generate the timing signal for indicating the release of the resonant state timing, and may sequentially transmit the timing signal thus generated to the external receiving apparatus. In addition, the timing signal generated by the timer unit may be superimposed on the image signals of the image in the body to be sequentially transmitted to the external receiving apparatus.

Further, the imaging unit is illustrated as one example of the execution unit (namely, execution unit of a function for synchronizing the resonant state release timing with the operation timing) of the function of the capsule medical device, which is repeatedly executed at a predetermined time interval in the first embodiment and the modified embodiment of the present invention, but not limited to this, the function executing unit of the capsule medical device may be a transmitting unit for sequentially transmitting the image signal, or may be an in-vivo information acquiring unit for periodically acquiring in-vivo information (temperature, pH value, body tissue, and the like) of the subject.

Moreover, the resonant state and the non-resonant state of the LC resonance circuit 27 are switched depending on the comparison result of the comparator 73 for comparing the signal from the demodulation circuit 64*c* with the reference signal from the reference signal generator 72 in the second embodiment of the present invention, but not limited to this, a comparator circuit having a circuit configuration using an AD converter may be incorporated in the capsule medical device 42 in place of the comparator 73, the external signal received by the LC marker 24*a* may be inputted into the AD converter of the comparator circuit to compare the output signal level last time with the output signal level this time by the AD converter, and when the difference between the output signal level last time and the output signal level this time of the AD converter is less than a specified value, it may be determined that there is the request of the resonant state release to thereby release the resonant state of the LC resonance circuit 27 for a predetermined period. In this case, it is possible to reduce the width of the magnetic field change of the drive coils 10a to 10c upon transmitting the request signal of the resonant state release to the capsule medical device 42, thus allowing the driving magnetic field of the drive coils 10a to 10c to be generated more stably.

Further, the magnetic field strength detection value in the three-dimensional space S is illustrated as the magnetic field detection data of the magnetic field detector 13 in the first and second embodiments, and the modified embodiment of the present invention, but not limited to this, the magnetic field detection data of the magnetic field detector 13 may be magnetic field information, such as a phase of the magnetic field in the three-dimensional space S or the like.

Moreover, there is used the position detecting system that detects the position/direction information of the capsule medical device 42 that moves the inside of the subject by peristalsis in the second embodiment of the present invention, but not limited to this, there may be used a position detecting system that incorporates a magnet in the capsule medical device 42, is further provided with the magnetic induction unit 6 for magnetically inducing this capsule medical device 42 incorporating the magnet therein, and detects the position/direction information of the capsule medical device 42 magnetically induced by this magnetic induction unit 6, as illustrated in the aforementioned modified embodiment of the first embodiment.

Further, the request signal of the resonant state release is generated and outputted at a predetermined time interval in the second embodiment of the present invention, but not limited to this, information (namely, information for requesting the calibration processing) for requesting the resonant state release of the LC resonance circuit 27 of the capsule medical device 42 may be inputted into the control unit 59 by the input unit 16 at a desired timing, and the request signal of the resonant state release may be generated and outputted whenever this information is inputted into the control unit 59.

Moreover, the request signal of the resonant state release is transmitted using the drive coils 10a to 10c as the transmission antenna in the second embodiment of the present invention, but not limited to this, a transmission antenna for transmitting the request signal of the resonant state release may be provided independently.

Further, the capsule medical device 42 receives the request signal of the resonant state release using the LC resonance circuit 27 as the receiving antenna in the second embodiment of the present invention, but not limited to this, a receiving antenna for receiving the request signal of the resonant state release may be provided independently.

Moreover, the capsule medical device is illustrated as one example of the detecting body for detecting the position/direction information inside the three-dimensional space S in the first and second embodiments, and the modified embodiment of the present invention but not limited to this, the detecting body of the position detecting system in accordance with the present invention may be any detecting body, as long as it is a detecting body incorporating the resonance magnetic field generator 24 and the function executing unit illustrated in the first embodiment, or the resonance magnetic field generator 64 illustrated in the second embodiment. In this case, such a detecting body is not limited to medical devices in particular.

Further, the capsule medical device (namely, capsule endoscope) for capturing the image in the body of the subject is illustrated as the capsule medical device which is one example of the detecting body in the first and second embodiments, and the modified embodiment of the present invention, but not limited to this, the capsule medical device as the detecting body described above may be a capsule-type pH measuring device for measuring pH in the living body, may be a capsule-type medicine administration device provided with a function of spraying or injecting medicines in the living body, or may be a capsule-type extraction device for extracting substances in the living body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detecting system comprising:
a magnetic field generator configured to generate a magnetic field in a three-dimensional space;
a detecting body configured to be introduced into the three-dimensional space, the detecting body comprising:
a resonance circuit configured to resonate with the magnetic field of the magnetic field generator to generate a resonance magnetic field,
a current bypass circuit connected in parallel to the resonance circuit to form an alternative path of a current in the resonance circuit, and
a resonance control circuit configured to control a current flow through the current bypass circuit to switch a resonant state and a non-resonant state of the resonance circuit;
a magnetic field detector configured to detect:
an environmental magnetic field to thereby generate detection data of the environmental magnetic field, the environmental magnetic field being a magnetic field in the three-dimensional space excluding the resonance magnetic field, and including at least a magnetic field of the magnetic field generator when the resonance control circuit switches the resonance circuit to the non-resonant state, and
a spatial magnetic field in the three-dimensional space to thereby generate detection data of the spatial magnetic field, the spatial magnetic field including the environmental magnetic field and the resonance magnetic field when the resonance control circuit switches the resonance circuit to the resonant state;
a position/direction calculating unit configured to perform position/direction calculating processing for calculating a position and a direction of the detecting body based on a detection data of the resonance magnetic field obtained by subtracting the detection data of the environmental magnetic field from the detection data of the spatial magnetic field; and
a control unit configured to acquire the detection data of the environmental magnetic field to perform update processing on the detection data of the environmental magnetic field if the resonance circuit is in the non-resonant state, to acquire the detection data of the spatial magnetic field if the resonance circuit is in the resonant state, and to cause the position/direction calculating unit to execute the position/direction calculating processing using the detection data of the spatial magnetic field thus acquired and the detection data of the environmental magnetic field which is subjected to the update processing.

2. The position detecting system according to claim 1, wherein
the detecting body is provided with
a function executing unit that repeatedly executes a predetermined function at a predetermined time interval, and
a transmitting unit that wirelessly transmits a timing signal for indicating a timing when the resonance circuit switches to the non-resonant state, whenever the function executing unit executes the predetermined function;
whenever the function executing unit executes the predetermined function, the resonance control circuit switches the resonance circuit to the non-resonant state to maintain the non-resonant state during a predetermined maintaining period; and
the control unit acquires the timing signal, and at each time of acquiring the timing signal, acquires one or more pieces of detection data of the environmental magnetic field within the predetermined maintaining period to thereby perform the update processing on the detection data of the environmental magnetic field.

3. The position detecting system according to claim 2, further comprising:
a receiving apparatus configured to receive at least the timing signal wirelessly transmitted by the transmitting unit and to output the received timing signal to the control unit,
wherein the control unit is further configured to acquire the timing signal via the receiving apparatus.

4. The position detecting system according to claim 2, wherein the control unit is further configured to:
make a piece of the detection data of the environmental magnetic field acquired upon start of the predetermined maintaining period and a piece of the detection data of the environmental magnetic field acquired upon completion thereof, invalid from a plurality of pieces of the detection data of the environmental magnetic field acquired within the predetermined maintaining period, and
perform the update processing on the rest of the detection data of the environmental magnetic field.

5. The position detecting system according to claim 2, wherein the predetermined maintaining period is more than twice the acquisition period of the detection data of the environmental magnetic field by the control unit.

6. The position detecting system according to claim 3, wherein
the detecting body is a capsule medical device introduced into the inside of a body of a subject,
the function executing unit is an in-vivo information acquiring unit for sequentially acquiring in-vivo information on the subject at the predetermined time interval,
the transmitting unit transmits a radio signal including the in-vivo information acquired by the in-vivo information acquiring unit and the timing signal,
the receiving apparatus receives the radio signal to extract the in-vivo information and the timing signal included in the radio signal, and outputs thus extracted timing signal to the control unit.

7. The position detecting system according to claim 6, wherein
the in-vivo information acquiring unit is an imaging unit for capturing an image in the body of the subject, which is the in-vivo information, and
the timing signal is a synchronizing signal of the image in the body captured by the imaging unit.

8. The position detecting system according to claim 1, wherein the control unit controls the resonance control circuit to switch the resonant state and the non-resonant state of the resonance circuit at a desired timing.

9. The position detecting system according to claim 8, wherein
the control unit is provided with a request signal generator for generating a request signal to request release of the resonant state of the resonance circuit at a desired timing,
whenever the request signal generator generates the request signal, the magnetic field generator transmits the request signal to the detecting body,
the resonance control circuit acquires the request signal transmitted by the magnetic field generator, switches the resonant state of the resonance circuit to the non-resonant state at an acquisition timing of the request signal, and maintains the non-resonant state during the predetermined maintaining period,
whenever the request signal generator generates the request signal, the control unit acquires one or more pieces of detection data of the environmental magnetic field within the predetermined maintaining period to thereby perform the update processing on the detection data of the environmental magnetic field.

10. The position detecting system according to claim 9, wherein the request signal generator sequentially generates the request signal at a predetermined time interval.

11. The position detecting system according to claim 9, further comprising an input unit for inputting instruction information to instruct the release of the resonant state of the resonance circuit,
wherein whenever the instruction information is inputted by the input unit, the request signal generator generates the request signal.

12. The position detecting system according to claim 9, wherein the resonance circuit receives the request signal transmitted by the magnetic field generator, and outputs thus received request signal to the resonance control circuit.

13. The position detecting system according to claim 9, wherein the resonance control circuit is provided with a timer circuit for maintaining a current flow through the current bypass circuit from an acquisition timing of the request signal until a predetermined time elapses to thereby maintain the non-resonant state of the resonance circuit during the predetermined maintaining period.

14. The position detecting system according to claim 9, wherein the control unit makes the detection data of the environmental magnetic field acquired upon start of the predetermined maintaining period and the detection data of the environmental magnetic field acquired upon completion thereof invalid among one or more pieces of detection data of the environmental magnetic field acquired within the predetermined maintaining period, and performs the update processing on the rest of the detection data of the environmental magnetic field.

15. The position detecting system according to claim 9, wherein the predetermined maintaining period is more than twice the acquisition period of the detection data of the environmental magnetic field by the control unit.

16. The position detecting system according to claim 8, wherein the detecting body is a capsule medical device introduced into the inside of a body of a subject.

17. The position detecting system according to claim 16, wherein the capsule medical device is provided with
- an in-vivo information acquiring unit for acquiring the in-vivo information of the subject, and
- a transmitting unit for wirelessly transmitting to the outside the in-vivo information acquired by the in-vivo information acquiring unit.

18. The position detecting system according to claim 17, further comprising a receiving apparatus for receiving the in-vivo information wireles sly transmitted by the transmitting unit,
- wherein the in-vivo information acquiring unit is an imaging unit for capturing an image in the body of the subject, which is the in-vivo information, and
- the transmitting unit wirelessly transmits to the receiving apparatus the image in the body of the subject captured by the imaging unit.

* * * * *